(12) United States Patent
Radcliffe et al.

(10) Patent No.: US 12,727,890 B2
(45) Date of Patent: Sep. 8, 2026

(54) UNICONDYLAR CUTTING BLOCK

(71) Applicant: DEPUY IRELAND UNLIMITED COMPANY, County Cork (IE)

(72) Inventors: Sarah Radcliffe, Leeds (GB); Sheetal Sanak, Leeds (GB); David Wolfson, Leeds (GB); James Barnett, Leeds (GB); Daniel Hoeffel, Warsaw, IN (US); Kevin Amesbury, Leeds (GB); Robert Freeman, Leeds (GB); Mark Reason, Leeds (GB)

(73) Assignee: DEPUY IRELAND UNLIMITED COMPANY LOUGHBEG INDUSTRIAL ESTATE, Ringaskiddy (IE)

( * ) Notice: Subject to any disclaimer, the term of this patent is extended or adjusted under 35 U.S.C. 154(b) by 635 days.

(21) Appl. No.: 17/999,982

(22) PCT Filed: May 28, 2021

(86) PCT No.: PCT/EP2021/064349
§ 371 (c)(1),
(2) Date: Nov. 28, 2022

(87) PCT Pub. No.: WO2021/239947
PCT Pub. Date: Dec. 2, 2021

(65) Prior Publication Data

US 2023/0293188 A1 Sep. 21, 2023

(30) Foreign Application Priority Data

May 29, 2020 (GB) ..................................... 2008131

(51) Int. Cl.

| | |
|---|---|
| ***A61B 17/15*** | (2006.01) |
| ***A61F 2/38*** | (2006.01) |
| ***A61F 2/46*** | (2006.01) |

(52) U.S. Cl.
CPC .............. *A61B 17/155* (2013.01); *A61F 2/38* (2013.01); *A61F 2/4657* (2013.01); *A61F 2002/3895* (2013.01); *A61F 2002/4661* (2013.01)

(58) Field of Classification Search
CPC ............................ A61B 17/155; A61B 17/157
See application file for complete search history.

(56) References Cited

U.S. PATENT DOCUMENTS

| | | |
|---|---|---|
| 4,524,766 A | 6/1985 | Peterson |
| 4,738,253 A | 4/1988 | Buechel et al. |

(Continued)

FOREIGN PATENT DOCUMENTS

| | | |
|---|---|---|
| CA | 2449336 A1 | 5/2004 |
| CA | 2489522 A1 | 7/2005 |

(Continued)

OTHER PUBLICATIONS

PCT Search Report From Corresponding PCT Application No. PCT/EP2021/064349 (Published as WO2021/239947) Dated Aug. 26, 2021, 4 Pages.

(Continued)

*Primary Examiner* — Andrew Yang

(57) ABSTRACT

A unicondylar posterior cutting block, method of use and kit of surgical components are provided, with the cutting block comprising: a base which is mountable on a resected proximal tibial surface of a knee of a patient in use; and a body pivotally attached to the base, the body including an alignment formation arranged to align with a marking on a femur in use, the body defining a cutting guide therein for receiving a cutting instrument to make a unicondylar posterior cut in the femur and wherein moving the alignment formation to align with the marking on the femur causes the body to rotate relative to the base and to tilt the cutting guide relative (Continued)

to the base. Different bases offer different cut positions and rotation of the base offers further different cut positions.

20 Claims, 12 Drawing Sheets

(56) References Cited

U.S. PATENT DOCUMENTS 5,597,379 A 1/1997 Haines
5,669,914 A 9/1997 Eckhoff
5,776,137 A 7/1998 Katz
7,060,074 B2 6/2006 Rosa
7,329,260 B2 2/2008 Auger
7,658,741 B2 2/2010 Claypool et al.
8,057,478 B2 11/2011 Kuczynski
8,167,888 B2 5/2012 Steffensmeier
9,216,026 B2 12/2015 Reeve
9,681,963 B2 6/2017 Leslie
9,974,547 B2 5/2018 Lin
10,448,960 B2 10/2019 Freiberg
12,232,747 B2 2/2025 Zaima
2003/0018338 A1* 1/2003 Axelson, Jr. ......... A61B 17/155 606/89
2003/0045883 A1* 3/2003 Chow .................... A61B 17/15 606/88
2005/0149037 A1 7/2005 Steffensmeier
2007/0005073 A1 1/2007 Claypool et al.
2007/0233140 A1 10/2007 Metzger
2010/0016859 A1 1/2010 Plassky et al.
2010/0168589 A1 7/2010 Banet et al.
2014/0257310 A1 9/2014 Trachsler et al.
2016/0089167 A1 3/2016 Lin
2016/0367373 A1 12/2016 Samuelson et al.
2017/0135708 A1 5/2017 Jaumard et al.
2019/0231365 A1 8/2019 Steensen et al.

FOREIGN PATENT DOCUMENTS

CN 102596107 A 7/2012
EP 0709061 B1 7/2003
JP 2001525536 A 12/2001
JP 2013526321 A 6/2013
JP 2015500674 A 1/2015
WO 2003045256 A2 6/2003
WO 2018189128 A1 10/2018

OTHER PUBLICATIONS

GB Search Report From Corresponding GB Patent Application GB2008131.1 Dated Nov. 24, 2020, 1 Page.
Sigma High Performance Partial Knee Unicondylar Surgical Technique, 140082-200512 DSUS/EMEA, DSUS/JRC/1114/0582 Rev. 3, 2017, 2019, 2020, 28 Pages.
Australian Examination Report for Corresponding Patent Application No. 2021278309 Dated Jan. 8, 2026, 3 Pages.
Japanese Decision To Grant (Including Translation) for Corresponding Japanese Application No. 2023-516845, Dated Jan. 17, 2025, 5 Pages.
Chinese Office Action and Search Report Translation for Corresponding Chinese Application No. 202180050088.6, Dated Jan. 22, 2026, 10 Pages.
Chinese Decision To Grant for Corresponding Chinese Application No. 202180050088.6, Dated Jun. 12, 2026, 5 Pages.

* cited by examiner 162
164
160
176
174
172
166
170
168
162
160
172
178
176
166
170
168

162
164
160
180
178
176
174
168
182

Figure 11
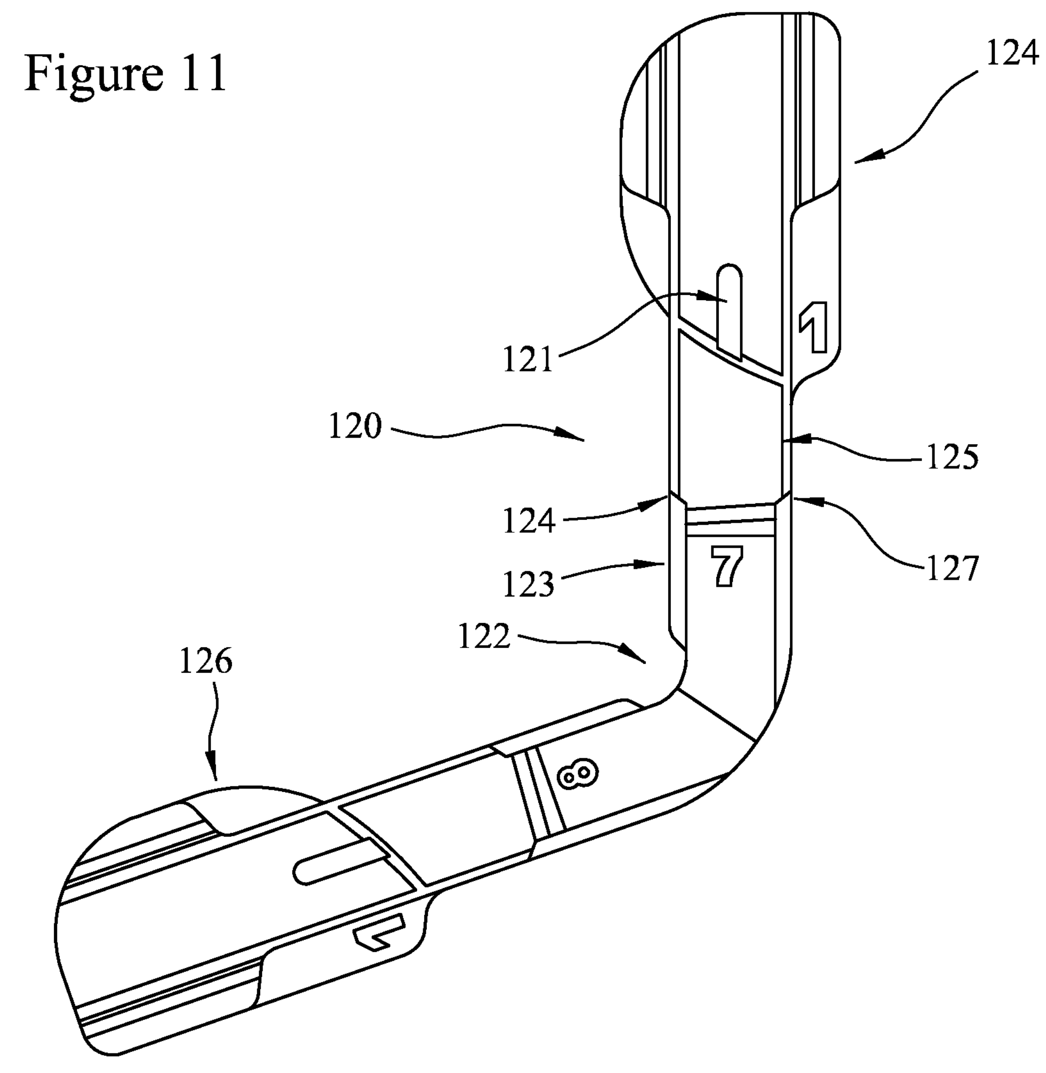
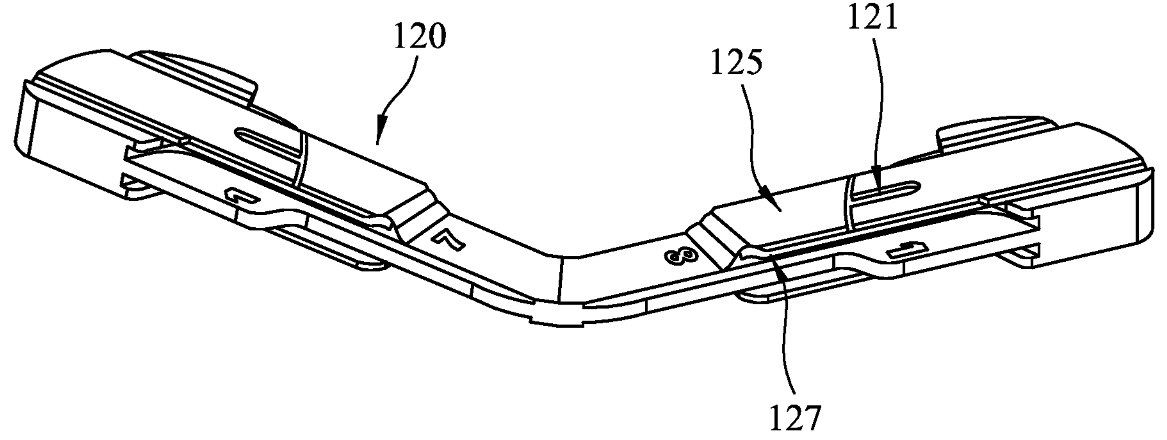
Figure 12

UNICONDYLAR CUTTING BLOCK

This application claims priority under 35 U.S.C. § 371 to International Patent Application No. PCT/EP2021/064349, entitled "Unicondylar Cutting Block" and filed on May 28, 2021, which claimed priority to Great Britain Patent Application No. GB2008131.1, which was filed on May 29, 2020. The entirety of each of those application is incorporated herein by reference.

TECHNICAL FIELD

The present disclosure relates to surgical instruments and methods, and in particular to surgical instruments and methods for use in a partial knee replacement procedure.

BACKGROUND

There are two general types of knee replacement procedures. A first is total knee replacement (TKR) procedures in which both condyles and the entire proximal tibia are replaced with respective prosthetic components to replace the entire. A second is partial or unicompartmental knee replacement procedures in which only a one of the condyles of the femur and the corresponding part of the proximal tibia, either the medial part or the lateral part, are replaced with respective prosthetic components.

An aspect of both types of procedure is making tibial cuts which largely define the position of the tibial prosthetic components on the tibia and the making of femoral cuts which largely define the position of the femoral prosthetic component relative to the femur. Often, cutting blocks are used to aid the making of such cuts and include some kind of guide to help guide a cutting instrument such as a powered bone saw or similar. A the cutting block is attached to the bone at some position and the position of the cutting block the largely defines where the cut is made, although some cutting blocks can also include adjustment mechanisms to allow the guide to move relative to the bone.

The positioning of the cuts is an important factor in the success of a knee replacement procedure and there are numerous degrees of freedom including the position of the tibial cuts relative to the tibia, the position of the femoral cuts relative to the femur and then the positions of the tibial and femoral cuts relative to each other.

The knee joint also includes various soft tissue structures and the impact of the positioning of the prosthetic components on the soft tissue structure also should be taken into account. For example, some surgeons perform soft tissue release if the resulting prosthetic knee leads to too much tension in the soft tissue structures, e.g. ligament release. In other instances, soft tissues may be too lax and so the surgeon may introduce shims or spacers to expand the knee gap to increase the tension in the soft tissue structures.

SUMMARY

The present disclosure is directed to surgical instruments, apparatus, kits of parts and methods relating to unicondylar knee replacement procedures which may improve the ability to make femoral cuts which take into account the impact on soft tissue structures.

A first aspect of the present disclosure provides a unicondylar posterior cutting block comprising: a base which is mountable on a resected proximal tibial surface of a knee of a patient in use; and a body pivotally attached to the base, the body including an alignment formation arranged to align with a marking on a femur in use, the body defining a cutting guide therein for receiving a cutting instrument to make a unicondylar posterior cut in the femur and wherein moving the alignment formation to align with the marking on the femur causes the body to rotate relative to the base and to tilt the cutting guide relative to the base.

The body may be connected to the base by a pivot defining an axis of rotation.

The base may include a curved member over which the body rides or cams when pivoting.

The curved member may have a non-constant radius of curvature. The pivot may be translatable relative to the base as the body rides or cams over the curved member.

The curved member may have a first shoulder at a first end and/or a second should at a second end.

The body may include a resilient biasing member arrange to maintain contact between the curved member and a part of the body.

The body may include a fixing arranged to capture the curved member within a part of the body.

The formation may define an elongate slot extending along a slot axis. The slot axis may pass through the axis of rotation. The formation may define a through aperture, such as a circular cross-sectioned aperture, for instance suitable for receiving a pin.

A rear face of the cutting block may define a first plane and the cutting guide may define a second plane. The first plane and the second plane may subtend an acute angle of 80° or less. The acute angle may be 75°.

The body may define an aperture extending therethrough for receiving a bone pin.

The base may include feet by which the base is releasably attachable to a tibial spacer.

The first aspect may include any of the features, options and possibilities set out elsewhere in this document, including in the other aspects.

A second aspect of the disclosure provides a kit of surgical instrumentation comprising: the unicondylar posterior cutting block of the first aspect and a tibial spacer including an attachment formation arranged to be engaged by the feet of the base to permit the base to be releasably mounted on the tibial spacer.

The tibial spacer may have a longitudinal axis and the attachment formation may be further configured to permit the base to be slid along the longitudinal axis of the tibial spacer.

The kit of surgical instrumentation may further comprise a plurality of tibial spacers, wherein each tibial spacer has a different thickness and/or a different size corresponding to a different size of tibial implant.

The tibial spacer may include a tibial spacer block and wherein the tibial spacer block may have an indicium indicating a centre line of the spacer block The kit of surgical instrumentation may further comprise a further unicondylar posterior cutting block defining a further cutting guide, and wherein the further cutting guide is positioned to make a posterior cut in the femur at a more anterior position than said unicondylar posterior cutting guide.

The kit of surgical instrumentation may further comprise a unicondylar distal cutting block having a distal cutting guide and further feet, and wherein the unicondylar distal cutting block is releasably mountable on the tibial spacer by the further feet engaging the attachment formation of the tibial spacer.

The kit of surgical instrumentation may further comprise a further unicondylar distal cutting block defining a further distal cutting guide, and wherein the further distal cutting guide is positioned to make a distal cut in the femur at a more distal position than said unicondylar distal cutting guide.

The distal cutting block and the further distal cutting block may each include a tail extending rearwardly and wherein said tails each have different thicknesses.

The second aspect may include any of the features, options and possibilities set out elsewhere in this document, including in the other aspects.

A third aspect of the present disclosure provides a method for making a unicondylar posterior cut to a femur of a knee of a patient, comprising: positioning a unicondylar posterior cutting block on a resected proximal tibial surface of a tibia of the knee of the patient and adjacent a distally resected condyle of a femur of the knee of the patient and with the knee in flexion, wherein the cutting block comprises a base and a body, the body being rotatable relative to the base and the body defining a cutting guide therein; aligning an alignment feature attached to the body with a marking on the femur to rotate the body relative to the base; fixing the body to the femur; and using the cutting guide to make a posterior femoral cut with a cutting tool.

The method may further comprise mounting the unicondylar posterior cutting block on a tibial spacer and wherein the tibial spacer is placed on the resected proximal tibial surface.

Mounting the cutting block on the tibial spacer may comprise: mounting the cutting block on the tibial spacer at a first position; and moving the cutting block along the tibial spacer form the first position toward the femur.

The method may further comprise: selecting a unicondylar posterior cutting block from a plurality of unicondylar posterior cutting blocks, each of the plurality of unicondylar posterior cutting blocks defining a respective cutting guide having a different position corresponding to a different anterior position or a different cut extent, such as cut depth or cut height, of the posterior cut.

The method may further comprise: mounting a unicondylar distal cutting block on the tibial spacer; and using the unicondylar distal cutting block to make a distal femoral cut.

The method may further comprise: selecting a unicondylar distal cutting block from a plurality of unicondylar distal cutting blocks, each of the plurality of unicondylar distal cutting blocks defining a respective cutting guide having a different position corresponding to a different distal position of the distal cut.

The method may further comprise: evaluating a flexion knee gap between a posterior part of a native condyle of the femur and a proximal resection of the tibia with the knee in flexion; evaluating an extension knee gap between a distal part of the native condyle and the proximal resection of the tibia with the knee in extension; and making a distal femoral cut at a distal position of the native condyle that will make the resulting knee gap in extension match the flexion knee gap.

The method may further comprise: evaluating a flexion knee gap between a posterior part of a native condyle of the femur and a proximal resection of the tibia with the knee in flexion; evaluating an extension knee gap between a distal part of the native condyle and the proximal resection of the tibia with the knee in extension; and making the posterior femoral cut at an anterior position of the native condyle that will make the resulting knee gap in flexion match the extension knee gap.

The method may further comprise: placing the knee in hyperflexion before aligning the alignment feature.

The method may further comprise: using a centre line on the tibial spacer to mark a vertical line on the femur when the knee is in flexion and/or extension.

The method, for instance of a further embodiment, may comprise each of the plurality of unicondylar posterior cutting blocks includes a graphical indicia indicative of the different cutting heights of the unicondylar posterior cutting blocks and further comprises: selecting a first unicondylar posterior cutting block including a first cutting guide and a first graphical indicia indicative of a cutting height of the first cutting guide, mounting the first unicondylar posterior cutting block on the tibial spacer and moving the first unicondylar posterior cutting block into contact with the femur. The method may include the first graphical indicia including one or more directional indicia elements. The method, for instance of the further embodiment, may further comprise: selecting a second unicondylar posterior cutting block including a second cutting guide and a second graphical indicia indicative of a cutting height of the second cutting guide, wherein the cutting height of the second cutting guide is greater than the cutting height of the first cutting guide and the second graphical indicia indicates that the cutting height of the second cutting guide is greater than the cutting height of the first cutting guide. The method further comprising:

selecting a third unicondylar posterior cutting block including a third cutting guide and a third graphical indicia indicative of a cutting height of the third cutting guide, wherein the cutting height of the third cutting guide is less than the cutting height of the first cutting guide and the third graphical indicia indicates that the cutting height of the third cutting guide is less than the cutting height of the first cutting guide.

The method, for instance the further embodiment, may provide cutting blocks having an anterior face with a superior edge and an inferior edge and the directional indicia element indicates a decrease in the cutting height with the directional indicia element pointing towards the inferior edge of the cutting block. The method, for instance the further embodiment, may provide that the directional indicia element indicates no change in the cutting height, for instance relative to a reference cutting height, with the directional indicia element being absent. The method, for instance the further embodiment, may provide that the directional indicia element indicates an increase in the cutting height with the directional indicia element pointing towards the superior edge of the cutting block. The method, for instance the further embodiment, may provide one or more cutting blocks provided with a graphical indicia also being provided with an alpha/numerical indica.

The method, for instance the further embodiment, may provide that the alpha/numerical indicia is indicative of at least a further characteristic of the cutting guide compared with the characteristic indicated by the graphical indicia.

The method, for instance the further embodiment, may provide that the alpha/numerical indicia is indicative of a magnitude of increase or of a magnitude of decrease in the cutting height or of no change in the cutting height. The method, for instance the further embodiment, may provide that the alpha/numerical indicia is non-indicative of an increase or of a decrease in the cutting height. The method, for instance the further embodiment, may provide that the graphical indicia include one or more further graphical indicia elements, the further graphical indicia element being an elongate element, such as a line. The method, for instance the further embodiment, may provide that the directional indicia element[s] are provided at or towards one end of the further graphical indicia element and/or the alpha/numerical indicia are provided at or towards one end of the further graphical indicia element. The method, for instance the further embodiment, may provide that the directional indicia element includes a triangle with an apex which is inferior to the base of the triangle to indicate a decrease and/or a triangle with an apex superior to the triangle base to indicate an increase.

The third aspect may include any of the features, options and possibilities set out elsewhere in this document, including in the other aspects.

A fourth aspect of the present disclosure provides a method for providing a prosthetic knee joint for a patient, the method including:

providing a plurality of cutting blocks of a type;

positioning a selected cutting block of the type adjacent the femur of the patient;

cutting away a portion of bone from the femur, guided by the selected cutting block;

wherein the method includes selecting the cutting block of the type, prior to positioning, from amongst the plurality of cutting blocks of the type;

wherein the plurality of cutting blocks of the type each have a configuration variable, the configuration variable having a value;

wherein the plurality of cutting blocks of the type include two or more cutting blocks of the type that have a difference in the value for the configuration variable relative to one another;

wherein the two or more cutting blocks of the type that have a difference in the value relative to one another each include one or more graphical indicia indicative of a least a part of the value for the configuration variable for the respective cutting block.

The graphical indicia may include one or more directional indicia elements.

The one or more graphical indicia may include a single directional indicia element.

The directional indicia element[s] may be indicative of an increase or of a decrease in the value or a part of the value. The directional indicia element[s] may be indicative of an increase or of a decrease in the value or a part of the value relative to a reference value, for instance a zero value. The directional indicia element[s] may be indicative of no change in the value or a part of the value relative to a reference value, for instance a zero value. The directional indicia element[s] may be indicative of no change in the value or a part of the value relative to a reference value, for instance a zero value, by being absent from the cutting block. The directional indicia element[s] may be non-indicative of a magnitude of increase or of a magnitude of decrease in the value or a part of the value. The directional indicia element[s] may be non-indicative of a magnitude of increase or of a magnitude of decrease in the value or a part of the value relative to a reference value, for instance a zero value.

The value or a part of the value represented by the graphical indicia, particularly by the directional indicia element, may indicate a decrease in the value or a part of the value when the cutting block has a configuration which will cut bone from the femur to decrease the gap between a part of the femur and a part of the tibia in at least one orientation of the tibia relative to the femur. The at least one orientation may include extension and/or flexion and/or hyperflexion.

The value or a part of the value represented by the graphical indicia, particularly by the directional indicia element, may indicate no change in the value or a part of the value when the cutting block has a configuration which will cut bone from the femur to leave the gap between a part of the femur and a part of the tibia in at least one orientation of the tibia relative to the femur, unchanged. The at least one orientation may include extension and/or flexion and/or hyperflexion.

The value or a part of the value represented by the graphical indicia, particularly by the directional indicia element, may indicate an increase in the value or a part of the value when the cutting block has a configuration which will cut bone from the femur to increase the gap between a part of the femur and a part of the tibia in at least one orientation of the tibia relative to the femur. The at least one orientation may include extension and/or flexion and/or hyperflexion.

The method may include providing the plurality of cutting blocks, with the cutting blocks having an anterior face with a superior edge and an inferior edge. The anterior face may be provided with a cutting slot through which a cutting element passes to cut the bone.

The graphical indicia, particularly the directional indicia element, may indicate a decrease in the value or a part of the value with the directional indicia element pointing towards the inferior edge of the cutting block. The directional indicia element may be provided closer to the inferior edge than the cutting slot. The directional indicia element may be provided further from the inferior edge than the cutting slot, for instance with the directional indicia element extend from a further graphical indicia element.

The graphical indicia, particularly the directional indicia element, may indicate no change in the value or a part of the value with the directional indicia element being absent.

The graphical indicia, particularly the directional indicia element, may indicate an increase in the value or a part of the value with the directional indicia element pointing towards the superior edge of the cutting block. The directional indicia element may be provided closer to the superior edge than the cutting slot. The directional indicia element may be provided further from the inferior edge than the cutting slot, for instance with the directional indicia element extend from a further graphical indicia element.

The configuration variable may be related to the separation between a cutting plane defined by the type of cutting block and a second plane. The second plane may be defined by a tibial spacer, for instance the inferior face of the spacer or the superior face of the spacer. The second plane may be defined by a surface of the tibia, for instance a resected surface. The configuration variable may be related to the extension gap between femur and tibia. The configuration variable may be related to the flexion gap between femur and tibia.

The method may include one or more cutting blocks provided with a graphical indicia also being provided with an alpha/numerical indica. The alpha/numerical indicia may be indicative of at least a part of the value for the configuration variable for the respective cutting block, for instance a further part of the value compared with the part of the value indicated by the graphical indicia. The alpha/numerical indicia may be a numerical indicia. The alpha/numerical indicia may be indicative of a magnitude of increase or of a magnitude of decrease in the value or a part of the value or of no change in the value or a part of the value. The alpha/numerical indicia may be indicative of a magnitude of increase or of a magnitude of decrease in the value or a part of the value relative to a reference value, for instance a zero value. The alpha/numerical indicia may be indicative of no change in magnitude relative to a reference value. The alpha/numerical indicia may be non-indicative of an increase or of a decrease in the value or a part of the value. The alpha/numerical indicia may be non-indicative of an increase or of a decrease in the value or a part of the value relative to a reference value, for instance a zero value.

The value or a part of the value represented by the alpha/numerical indicia, particularly by the numerical indicia, may be a magnitude of change. The value or a part of the value may be expressed in mm. The plurality of cutting blocks may provide a series of different magnitudes of change, for instance in 1 mm intervals. The value or a part of the value represented by the alpha/numerical indicia, particularly by the numerical indicia, may be a magnitude of change provided by the cutting block having a configuration which will cut bone from the femur to increase or decrease or leave unchanged the gap between a part of the femur and a part of the tibia in at least one orientation of the tibia relative to the femur. The at least one orientation may include extension and/or flexion and/or hyperflexion.

The graphical indicia may include one or more further graphical indicia elements.

The further graphical indicia element may be an elongate element, such as a line, for instance extending substantially parallel to a slot in the cutting block, such as a slot for a cutting element used to cut the femur.

The directional indicia element[s] may be provided at or towards one end of the further graphical indicia element. Alpha/numerical indicia may be provided at or towards one end of the further graphical indicia element, such as the other end to the directional indicia element[s].

The at least a part of the value may be a graphical indicia of whether the value is increased and/or is unchanged and/or is decreased. The at least a part of the value may be a graphical indicia that the value is increased, with the graphical indicia being a directional indication extending to one side of a further graphical indicial element, for instance away from the slot that receives a cutting element. The at least a part of the value may be a graphical indicia that the value is decreased, with the graphical indicia being a directional indication extending to one side of a further graphical indicial element, for instance towards the slot that receives a cutting element.

The directional indicia element may be a triangle, for instance a triangle with an apex which is inferior to the base, for instance to indicate a decrease. The directional indicia element may be a triangle, for instance a triangle with an apex superior to the base, for instance to indicate an increase.

The directional indicia element may be an up arrow extending superiorly. The directional indicia element may be a down arrow extending inferiorly. The directional indicia element may be an arrow head, such as an up arrow head extending superiorly or a down arrow head extending inferiorly.

The selecting may include the selection of one cutting block of the type from amongst two, three, four or more cutting blocks of the type. The selecting may be provided based upon a match between the value for the configuration variable of a cutting block with the value of the configuration variable for a cutting block that the user wishes to use in the method. The match may be determined by the user inspecting the value of the configuration variable. The match may be determined by the user inspecting one or more graphical indicia. The match may be determined by the user inspecting one or more alpha/numerical indicia. The match may be determined by the user inspecting one or more graphical indicia and one or more alpha/numerical indicia. The value may be a combination of the one or more graphical indicia and one or more alpha/numerical indicia.

The method may include selecting the one cutting block of the type from a plurality presented on a surface and/or in a surgical instrument tray. The method may include the one or more graphical indicia and/or one or more alpha/numerical indicia facing away from the surface and towards the user and/or out of the surgical instrument tray, for instance upwards, during selection.

The type of cutting block may be a first type of cutting block. The first type of cutting block may be posterior cutting block. The first type of cutting block may be a unicondylar posterior cutting block.

The configuration variable may be related to the separation between a cutting plane defined by the first type of cutting block and a second plane. The second plane may be defined by a tibial spacer, for instance the inferior face of the spacer or the superior face of the spacer. The second plane may be defined by a surface of the tibia, for instance a resected surface. The configuration variable may be related to flexion gap between femur and tibia.

The value may be one of a discrete set of values. The discrete set of values may include a intermediate value and one or more lower values and/or one or more higher values, those being the difference in the values.

The intermediate value may provide an intermediate level of laxity in flexion of the knee, for instance 1 mm of laxity. The intermediate value may provide a cutting plane 7 to 8 mm, such as 7.5 mm or 7.7 mm, above the second plane, such as the superior surface of the tibial spacer.

The one or more lower values may provide a lower level of laxity in flexion of the knee, for instance less than 1 mm. The one or more lower values may provide a cutting plane less than 7.5 mm above the second plane, for instance less than 7 mm, such as 6.7 mm or less.

The one or more higher values may provide a higher level of laxity in flexion of the knee, for instance greater than 1 mm of laxity, for instance 2 mm or more. The one or more higher values may provide a cutting plane more than 7.5 mm, or more than 7.7 mm, above the second plane, for instance 8.5 mm or more or 8.7 mm or more.

The positioning of the first type of cutting block may be on a resected proximal tibial surface of a tibia of the knee of the patient and/or adjacent a distally resected condyle of a femur of the knee of the patient. The knee may be in flexion.

The method may include the use of a posterior cutting block according to the first aspect. The method may include the first type of cutting block comprising a base and a body. The method may include the body being rotatable relative to the base and the body defining a cutting guide therein. The method may further include aligning an alignment feature attached to the body with a marking on the femur to rotate the body relative to the base. The method may further include fixing the body to the femur. The method may further include using the cutting guide to make a posterior femoral cut with a cutting tool.

The type of cutting block may be a second type of cutting block. The second type of cutting block may be a distal cutting block. The first type of cutting block may be a unicondylar distal cutting block.

The configuration variable may be related to the separation between a cutting plane defined by the second type of cutting block and a third plane. The third plane may be defined by a tibial spacer, for instance the inferior face of the spacer or the superior face of the spacer. The third plane may be defined by a surface of the tibia, for instance a resected surface. The configuration variable may be related to the extent of distalization for the femoral resection.

The value may be one of a discrete set of values. The discrete set of values may include a base value and one or more lower values, those being the difference in the values.

The base value may provide resurfacing of the femur. The base value may provide for resectioning of the femur where the flexion gap and the extension gap are balanced or within an acceptable range, for instance 0 mm to 2 mm difference. The base value may provide a cutting plane 6.5 to 7 mm, such as 6.7 mm, above the third plane, such as the superior surface of the tibial spacer.

The one or more lower values may provide for distalizing of the femoral resection. The one or more lower values may reduce the difference between the flexion gap and the extension gap. The one or more lower values may provide a cutting plane less than 6.5 mm above the second plane, for instance less than 6 mm for one cutting block, less than 5 mm for another cutting block and less than 4 mm for a further cutting block.

The positioning of the second type of cutting block may be on a resected proximal tibial surface of a tibia of the knee of the patient and/or adjacent a distally resected condyle of a femur of the knee of the patient. The knee may be in flexion.

The method may include the use of a distal cutting block, for instance a unicondylar distal cutting block. The distal cutting block may have a distal cutting guide and further feet. The distal cutting block may be releasably mountable on the tibial spacer by the further feet engaging the attachment formation of the tibial spacer. The method may further include fixing the distal cutting block to the femur. The method may further include using the cutting guide to make a distal femoral cut with a cutting tool.

The method may include the use of a second type of cutting block and then the use of a first type of cutting block. In particular, the method may include:

positioning a selected cutting block of the second type adjacent the femur of the patient;

cutting away a portion of bone from the femur;

wherein the method includes selecting the cutting block of the second type, prior to positioning, from a plurality of cutting blocks of the second type;

wherein the plurality of cutting blocks of the second type each have a configuration variable, the configuration variable having a value;

wherein the plurality of cutting blocks of the second type include two or more cutting blocks of the second type that have a difference in the value from one another with respect to the value of the configuration variable;

wherein the two or more cutting blocks of the second type that differ from one another include one or more graphical indicia indicative of a least a part of the value for the configuration variable for the respective cutting block of the second type.

The method may further include the use of a first type of cutting block after the use of the second type of cutting block.

The method may further comprise, after the use of the second type of cutting block:

positioning a selected cutting block of the first type adjacent the femur of the patient;

cutting away a portion of bone from the femur;

wherein the method includes selecting the cutting block of the first type, prior to positioning, from a plurality of cutting blocks of the first type;

wherein the plurality of cutting blocks of the first type each have a configuration variable, the configuration variable having a value;

wherein the plurality of cutting blocks of the first type include two or more cutting blocks of the first type that have a difference in the value from one another with respect to the value of the configuration variable;

wherein the two or more cutting blocks of the first type that differ from one another include one or more graphical indicia indicative of a least a part of the value for the configuration variable for the respective cutting block of the second type.

The method, for instance of a further embodiment, may comprise each of the plurality of unicondylar posterior cutting blocks includes a graphical indicia indicative of the different cutting heights of the unicondylar posterior cutting blocks and further comprises: selecting a first unicondylar posterior cutting block including a first cutting guide and a first graphical indicia indicative of a cutting height of the first cutting guide, mounting the first unicondylar posterior cutting block on the tibial spacer and moving the first unicondylar posterior cutting block into contact with the femur. The method may include the first graphical indicia including one or more directional indicia elements. The method, for instance of the further embodiment, may further comprise: selecting a second unicondylar posterior cutting block including a second cutting guide and a second graphical indicia indicative of a cutting height of the second cutting guide, wherein the cutting height of the second cutting guide is greater than the cutting height of the first cutting guide and the second graphical indicia indicates that the cutting height of the second cutting guide is greater than the cutting height of the first cutting guide. The method further comprising:

selecting a third unicondylar posterior cutting block including a third cutting guide and a third graphical indicia indicative of a cutting height of the third cutting guide, wherein the cutting height of the third cutting guide is less than the cutting height of the first cutting guide and the third graphical indicia indicates that the cutting height of the third cutting guide is less than the cutting height of the first cutting guide.

The fourth aspect may include any of the features, options and possibilities set out elsewhere in this document, including in the other aspects.

A fifth aspect of the present disclosure provides a posterior cutting block comprising: a base which is mountable on a resected proximal tibial surface of a knee of a patient in use; and a body, the body defining a cutting guide therein for receiving a cutting instrument to make a posterior cut in the femur; wherein the body has a configuration variable characteristic of the position of the cutting guide and the configuration variable has a value; wherein the body includes one or more graphical indicia indicative of a least a part of the value for the configuration variable for the respective cutting block.

The cutting block may be a unicondylar posterior cutting block. The cutting block may further comprise a body pivotally attached to the base. The cutting block may further comprise the body including an alignment formation arranged to align with a marking on a femur in use. The cutting block may further provide wherein moving the alignment formation to align with the marking on the femur causes the body to rotate relative to the base and to tilt the cutting guide relative to the base.

The fifth aspect may include any of the features, options and possibilities set out elsewhere in this document, including in the other aspects and particularly the fourth aspect.

A sixth aspect of the present disclosure provides a unicondylar distal cutting block comprising: a base section which is mountable on a resected proximal tibial surface of a knee of a patient in use; and a body section, the body section defining a cutting guide therein for receiving a cutting instrument to make a distal cut in the femur; wherein the body section has a configuration variable characteristic of the position of the cutting guide and the configuration variable has a value; wherein the body section includes one or more graphical indicia indicative of a least a part of the value for the configuration variable for the respective cutting block.

The cutting block may be a unicondylar distal cutting block.

The sixth aspect may include any of the features, options and possibilities set out elsewhere in this document, including in the other aspects and particularly the fourth aspect.

A seventh aspect of the disclosure provides a kit of surgical instrumentation comprising: a cutting block of the fifth aspect or a cutting block of the sixth aspect and a tibial spacer including an attachment formation arranged to be engaged by the feet of the base or base section to permit the base or base section to be releasably mounted on the tibial spacer.

The kit may further include a cutting block according to the other of the sixth aspect or fifth aspect. The kit may include a plurality of cutting blocks of a first type, such as a posterior cutting block, and/or a plurality of cutting blocks of a second type, such as distal cutting blocks.

The seventh aspect may include any of the features, options and possibilities set out elsewhere in this document, including in the other aspects and particularly the fourth aspect.

BRIEF DESCRIPTION OF THE DRAWINGS

Embodiments will now be described in detail, by way of example only, and with reference to the accompanying drawings, in which:

FIG. 11 shows a plan elevation of a sized tibial spacer of the surgical instrumentation illustrated in FIG. 1;

FIG. 12 is a perspective view of the sized tibial spacer illustrated in FIG. 11;

In the Figures of drawings, like items in the different Figures share common reference signs unless indicated otherwise.

DETAILED DESCRIPTION

Figure 1:
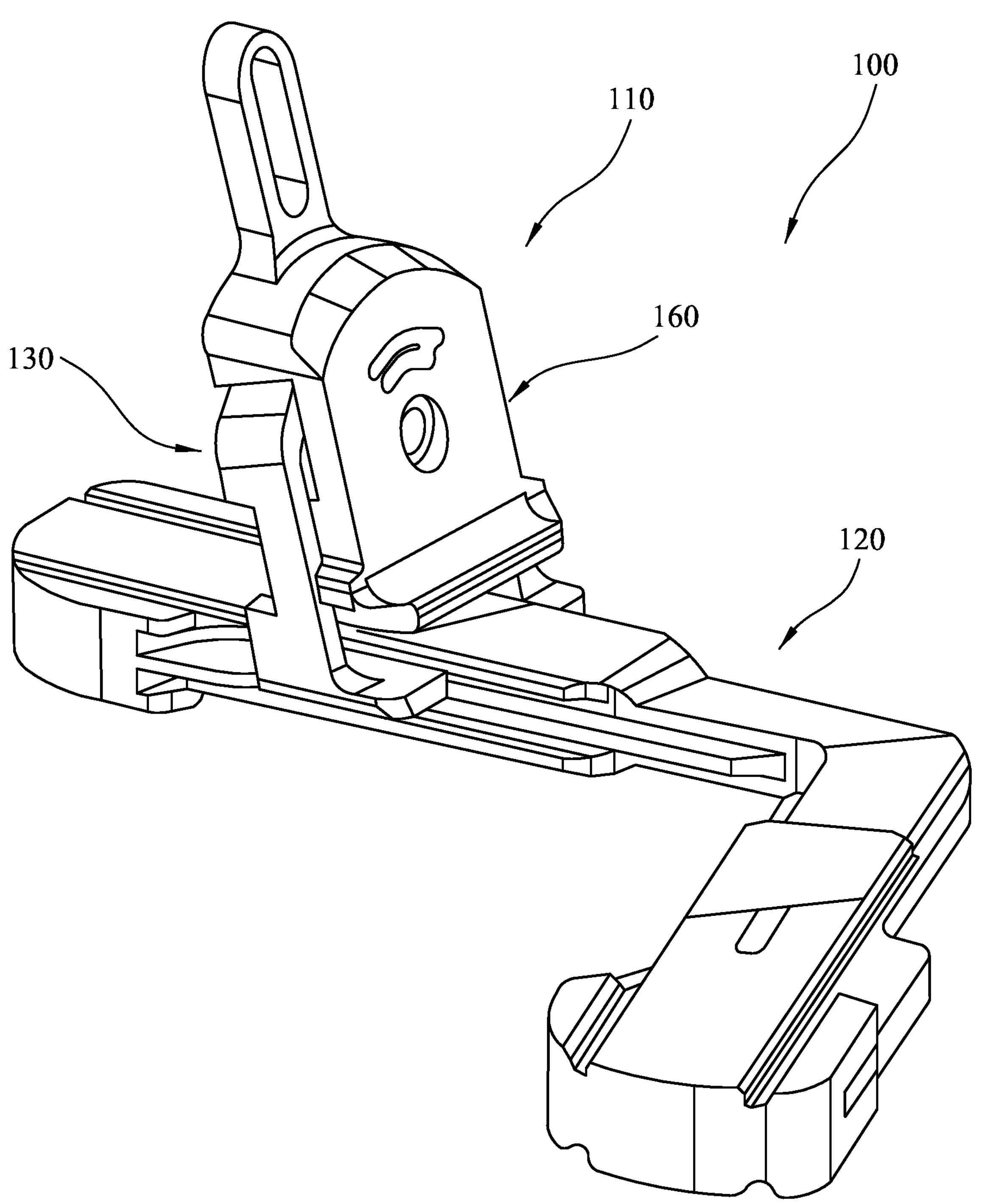
FIG. 1 shows a perspective view of an assembly of surgical instrumentation for making a unicondylar posterior cut.

With reference to FIG. 1 there is shown a perspective view of an assembly of surgical instrumentation 100 for use in making a unicondylar posterior cut during a partial knee replacement surgical procedure. The assembly 100 includes a cutting block 110 mounted on a tibial spacer 120. The cutting block 110 has two major components, a base 130 by which the cutting block is mounted indirectly on the resected tibia in use via a spacer block of the tibial spacer 120, and a body 160 which is pivotably connect to the base so that the body can pivot or rotate relative to the base 130.

Figures 2, 3, 4:
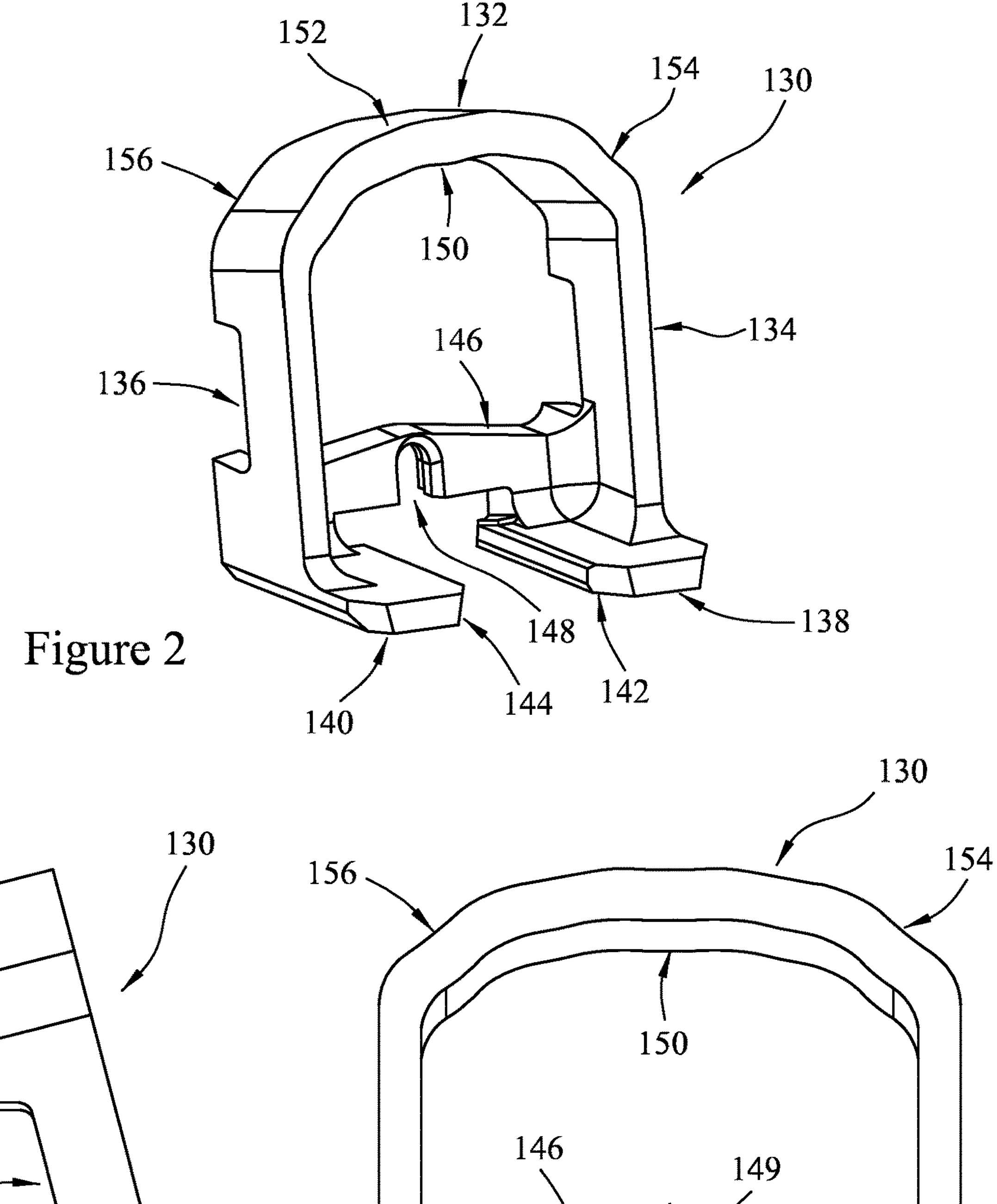
FIG. 2 shows a perspective view of a base of a unicondylar posterior cutting block of the instrumentation shown in FIG. 1.
FIG. 3 show a side elevation of the base shown in FIG. 2.
FIG. 4 shows a front elevation of the base shown in FIG. 2.

The base 130 is illustrated in FIGS. 2, 3 and 4. FIG. 2 shows a perspective view of the front of the base 130, FIG. 3 shows a side elevation of the base and FIG. 4 shows a front elevation of the base. As can be seen in FIGS. 2 to 4, the base 130 generally has the form of an arch and includes a curved member 132 extending between a first 134 and a second 136 side member or leg. Each leg ends in an inwardly directed foot, 138, 140. Each foot 138, 140 defines a respective rib 142, 144 for engaging respective slots defined in the tibial spacer as described in greater detail below.

The base 130 also includes a cross member 146 extending across the base and between the first 134 and second 136 legs. Cross member 146 defines a cavity 148 therein and which is arranged to receive a part of a pivot as described in greater detail below. Cavity 148 is defined by a curved closed end and a channel leading to the curved closed end. The cavity 148 is symmetric about a central line 149 along which a pivot can translate in use as described in greater detail below.

The curved member 132 has a complex shape. A central portion 150 has a slightly dished or bowed part relative to the adjacent parts of the curved member. The curved member generally has a shape defined by a spline and comprises adjacent portions of slightly increasing radius of curvature and then slightly decreasing radius of curvature, wherein the centres of the radii of curvature fall on the centre of the channel of the aperture 148. An upper surface 152 of the curved member 132 provides a camming surface over which a similarly shaped surface of the body rides in use. The curved member 132 also includes a first shoulder 154 and a second shoulder 156 to either side of the central arced portion formed by the portion of slightly reducing radius of curvature. These shoulders help to prevent the body binding against the curved member when it pivots relative thereto.

As can be seen in FIG. 3 the plane of the rear face of the base is generally inclined relative to the plane defined by cutting guide slot or the feet 138, 140. The acute angle formed between the plane of the base and the plane of the feet is approximately 75°.

Figures 5, 6, 7:
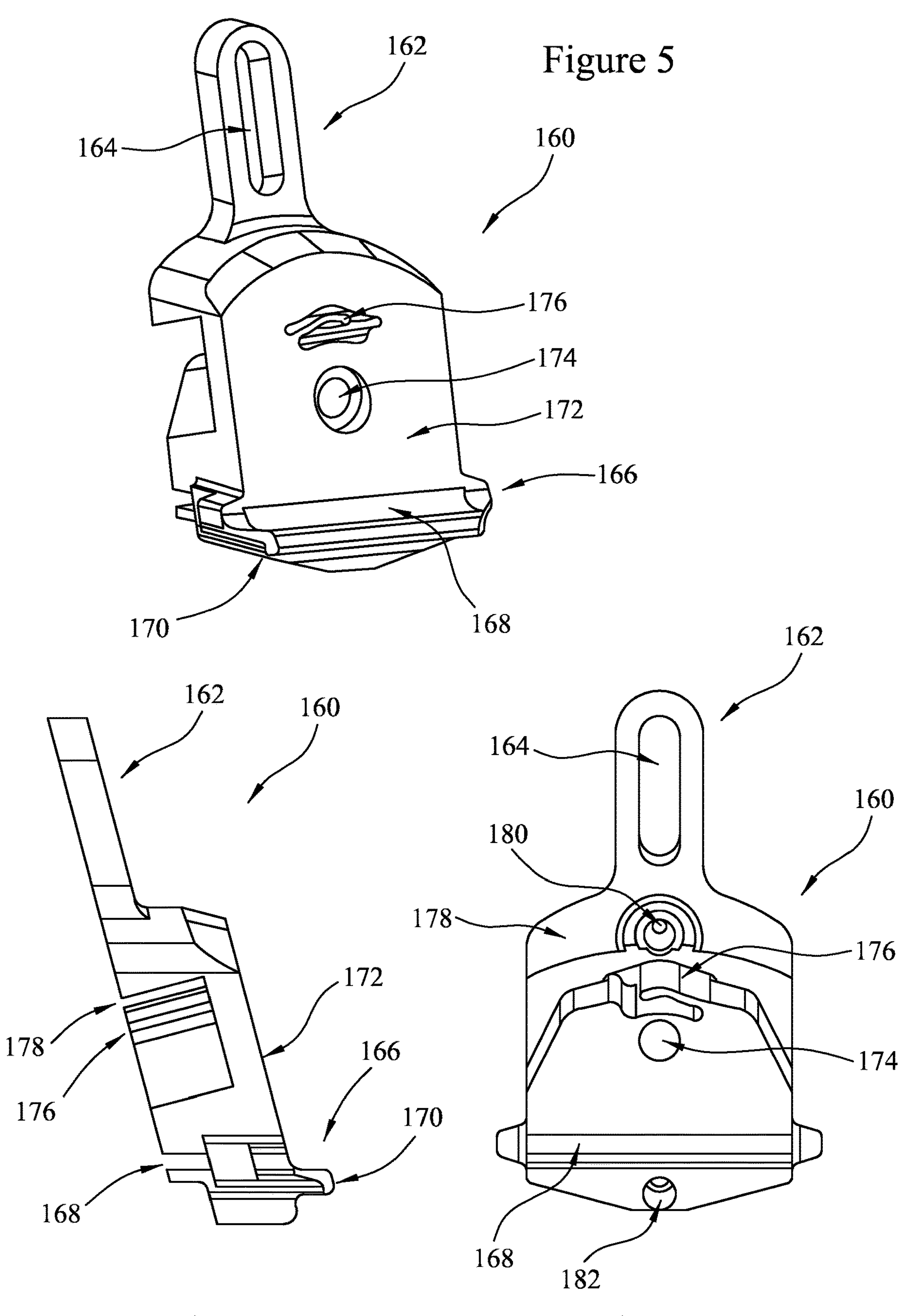
FIG. 5 shows a perspective view of a body of the unicondylar posterior cutting block of the instrumentation shown in FIG. 1.
FIG. 6 show a side elevation of the body shown in FIG. 5.
FIG. 7 shows a rear elevation of the body shown in FIG. 5.

The body 160 is illustrated in FIGS. 5, 6 and 7. FIG. 5 shows a perspective view of the front of the body 160, FIG. 6 shows a side elevation of the body and FIG. 7 shows a rear elevation of the body.

An elongate member 162 extends form an upper end of the body 160 and defines a slot 164 therein. The elongate slot 164 extends along a slot axis. As explained in greater detail below, slot 164 can be used to set the correct amount of rotation of the cutting guide by setting the slot parallel to a femoral condyle internal/external rotation line. A bone pin may then be inserted through slot 164 and into the distally resected femur, to fix the angle and prevent the body from moving. The body may be configured to rotate by up to 6 degrees relative to the base in each direction, i.e. +6 degrees and −6 degrees relative to a central aligned position. It is also possible, as shown in the FIGS. 22*a*, 22*b* and 22*c* embodiments, to provide a through aperture 504, rather than an elongate slot 164, in the elongate member 162. The through aperture 504 is used for the same purpose, to receive a bone pin once alignment is provided.

A lower portion 166 of the body 160 defines a slot 168 which passes through the body 160 and which provides a cutting guide for receiving a saw blade in use to make the unicondylar posterior cut. As illustrated in FIGS. 5 to 7, a lip 170 extends from a front face 172 of the body and flush with a lower surface of the cutting guide slot 168 in order to aid blade insertion. In other embodiments, lip 170 may be omitted and instead a recessed section may be provided adjacent the mouth of the cutting slot 168 again to aid blade insertion.

A bore 174 is defined by a central portion of the body 160 and passes therethrough to provide a pinning hole for optionally receiving a further bone pin if surgeons require further pinning options, depending on the bone quality.

As best illustrated by FIG. 7, which shows the rear of the body, the body 160 also includes a resilient biasing member in the form of a live spring 176 arranged adjacent an generally curved channel 178 defined in the rear of the body. An upper surface defining the channel 178 has a generally similar curved shape as the upper surface 152 of the curved member 132 of the base so that the body can ride over the curved member when received in curved channel 178. Live spring 176 is arranged to act against an under surface of the curved member to help remove play and provide rotational stability. A first threaded bore 180 is defined in the body adjacent and just above the curved channel 178. A second threaded bore 182 is defined in a lower part of the body below the cutting guide slot 168.

Similarly to the base, the plane of the body is inclined relative to the plane defined by the cutting guide slot 168, and by the same angle of inclination as the base. Hence, the acute angle subtended by the plane of the body and the plane of the cutting guide slot may be approximately 75°.

Figures 8, 9:
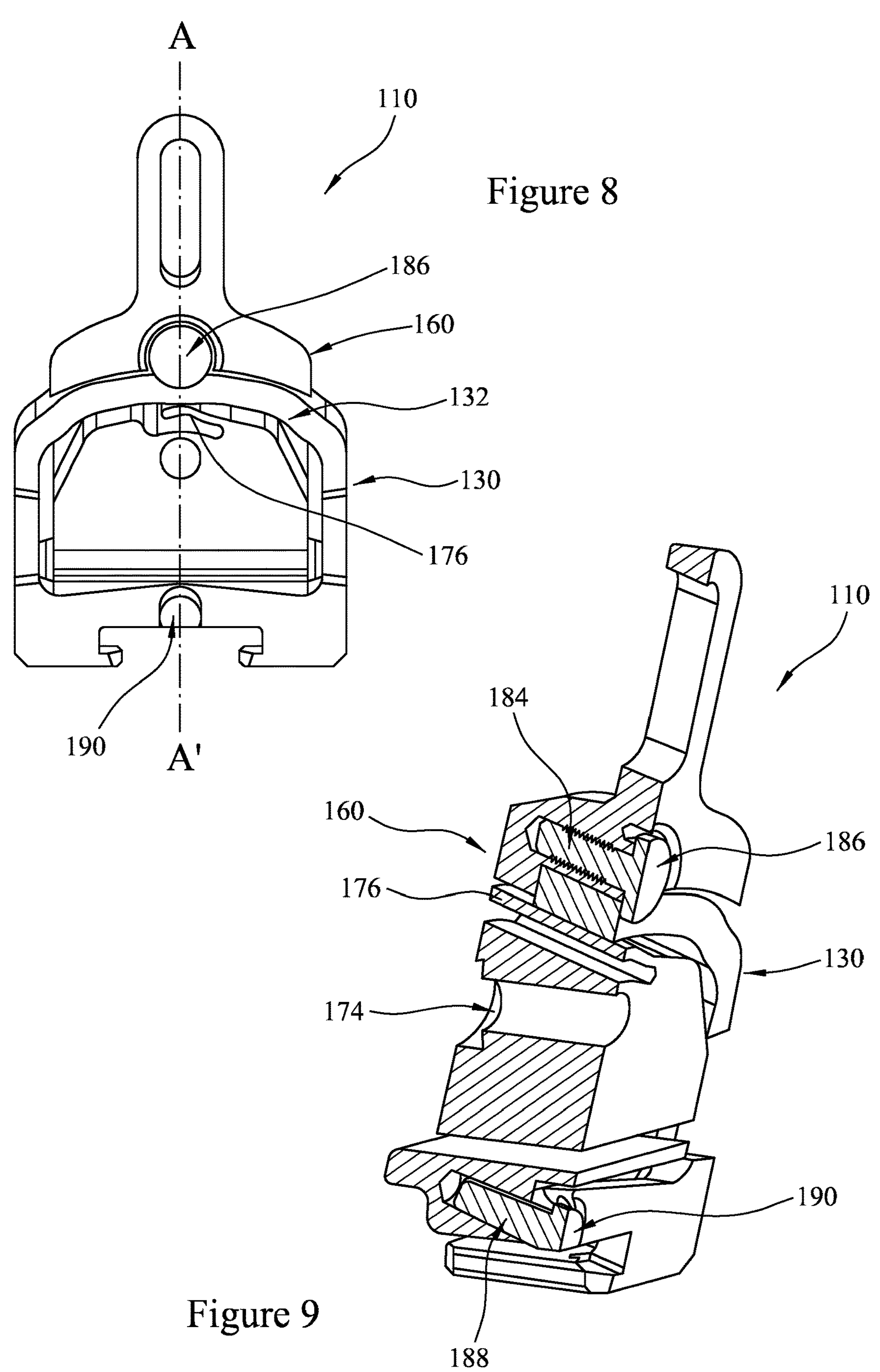
FIG. 8 shows a rear elevation of the unicondylar posterior cutting block comprising an assembly of the base of FIG. 2 and the body of FIG. 5.
FIG. 9 shows a perspective cross section view through the cutting block shown in FIG. 8 along line A-A'.

FIG. 8 shows a rear view of the unicondylar posterior cutting block 110 formed form the body 160 and the base 130 and FIG. 9 shows a perspective cross sectional view of the cutting block along line A-A' of FIG. 8. As best illustrated by FIG. 9, a first fixing 184 in the form of a threaded bolt with a head is received within the first threaded bore 180 in the body. The head 186 of the threaded bolt seats on the body and acts to capture the curved member 132 within the curved channel 178 of the body 160. As also illustrated in FIGS. 8 and 9, the live spring is compressed against the underside of the curved member to remove play between the body and base and improve rotation stability by urging the curved member against the body.

A second fixing 188 in the form of a threaded bolt with ahead 190 is received within the second threaded bore 182 in the lower part of the body. The second fixing 188 seats on the base and provides a pivot having a pivot axis and about which the body 160 can pivot or rotate relative to the base 130. Also, the second fixing 188 can translate along the central axis 149 (co-incident with line A-A') within channel 148. Hence, the pivot axis defines the centre of rotation of the body and which can translate along axis 149 as the body rotates relative to the base owing to the non-constant radius of curvature of the curved member 132. The shape of the curved member 132, described above, accounts for the geometry of the femoral implant to be used, and which also has a non-constant radius of curvature, and helps to maintain the desired joint gap or spacing as described in greater detail below.

Figure 10:
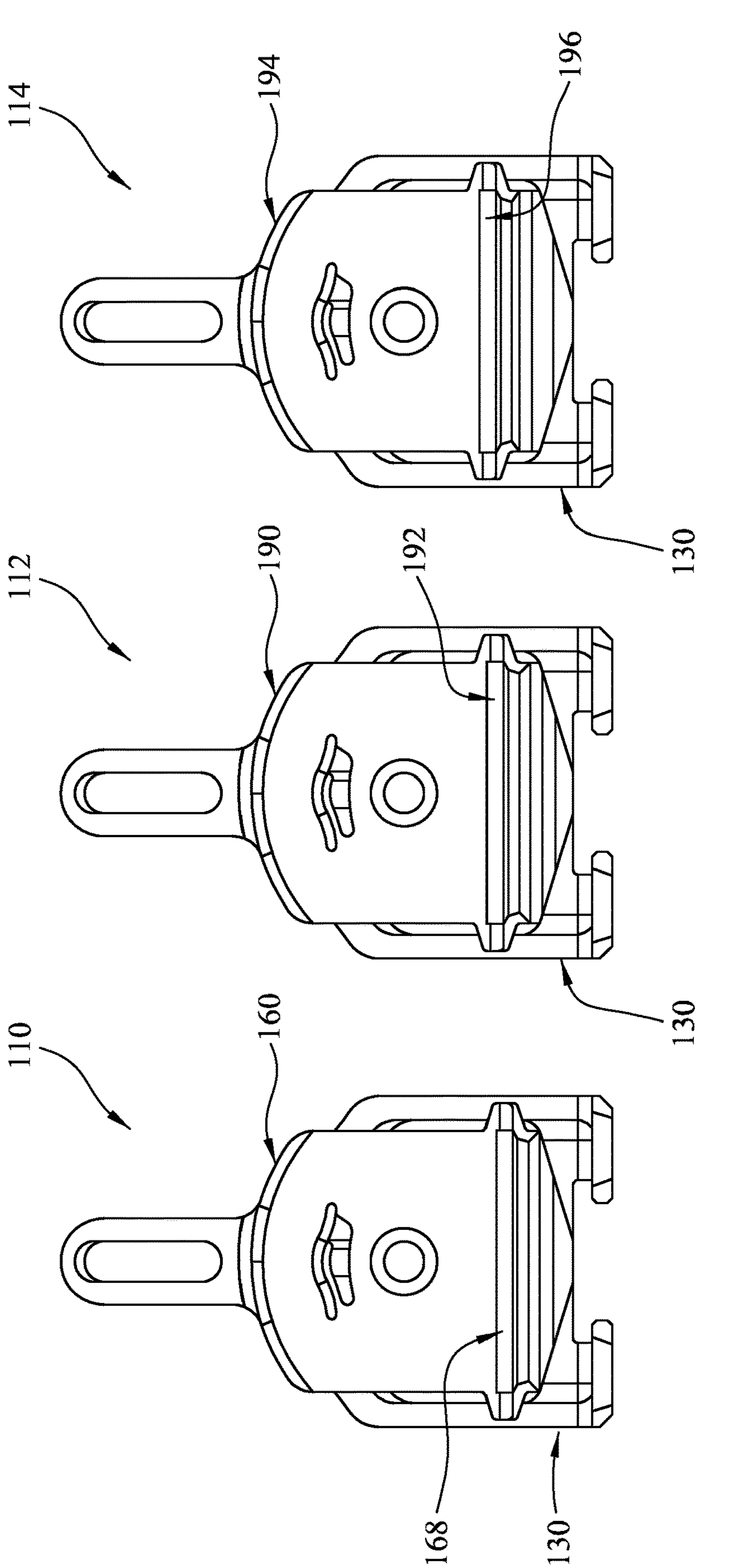
FIG. 10 shows front elevations of three cutting blocks each having a different body corresponding to a different amount of off set of the posterior cut.

The body 160 described so far has the cutting guide slot 168 at a position on the body giving rise to zero off set of femoral cut, i.e. 0 mm of offset. That is, the resulting femoral cut will have no off set and hence the femoral implant seated on that cut and the planned tibial component thickness will give rise to a particular knee gap. As illustrated in FIG. 10, the surgical instrumentation may include a plurality of cutting blocks 110, 112, 114 each having a different femoral cut offset. For example a first cutting block 110 which uses the base 130 and the body 160 may give rise to a 0 mm offset femoral cut height. A second cutting block 112 may use the same base 130 but a slightly different second body 190, which is generally similar to the first body 160, but in which the cutting guide slot 192 is displaced by approximately 1 mm compared to the first body, so as to provide a 1 mm off set femoral cut height. A third cutting block 114 may use the same base 130 but a slightly different third body 194, again generally similar to the first body 160, but in which the cutting guide slot 196 is displaced by approximately 2 mm compared to the first body 160, so as to provide a 2 mm off set femoral cut height.

As the positions of the cutting guide slots of the second and third bodies remove approximately 1 mm and 2 mm more femoral bone respectively than the first body, cutting blocks using these bodies may be used if the surgeon decides that the soft tissue tension might otherwise be too great and so wants to introduce some laxity into the soft tissue by increasing the separation between the proximal tibial cut and the posterior femoral cut. In other embodiments a greater or lesser number of cutting blocks with different bodies may be provided and/or the different cutting blocks may provide other different cut off sets and different amounts of offset may also be provided, e.g. 0 mm, 2 mm and 4 mm.

FIG. 11 shows a plan view of a tibial spacer 120 of the surgical instrumentation. Although having a boomerang type form in FIG. 11, the tibial spacer 120 may also have a linear or a right angled form in other embodiments. FIG. 12 shows a perspective view of the tibial spacer 120. The tibial spacer 120 has a handle or arm portion 122 and a first spacer block 124 at a first end and a second spacer block 126 at a second end. Each spacer block 124, 126 generally has the same shape and size as a corresponding tibial implant or prosthesis.

A partial tibial implant or prosthesis generally has a base part and a bearing surface often made of a polymer or similar. The base part may have different thicknesses. Also, tibial implants of different sizes are often provided so that the tibial implant may more closely match the anatomy of the patient. Hence, the tibial spacer 120 illustrated in FIGS. 11 and 12 has spacer blocks 124 and 126 both of the same size, and corresponding to the size of a smallest tibial implant. However, the spacer blocks 124 and 126 have different thicknesses. For example the first spacer block 124 may have a thickness of 7 mm (corresponding to the overall thickness of the intended tibial implant) while the second spacer block 126 may have a thickness of 8 mm, corresponding to the same size of tibial implant but with a greater base height. Hence, the instrumentation may include multiple tibial spacers similar to tibial spacer 120, but having further different thicknesses, e.g. 9 mm and 10 mm, or 6 mm and 5 mm. Also, the instrumentation may include multiple tibial spacers similar to tibial spacer 120, but having different sizes corresponding to other sizes of tibial implant, and multiple different thicknesses for each implant sizes. Hence the instrumentation may include a set of tibial spacers with a range of different thicknesses and for each different implant size.

The tibial spacer 120 illustrated in FIG. 11 is symmetric in the plane of FIG. 11 and hence can be used for left hand or right-hand knees.

As can be best seen in FIG. 11, the middle portion 123 of the handle 122 is less wide and then the handle develops into a raised portion 125 having formations extending laterally therefore and defining a respective slot 127, 129 on each side arranged to receive the ribs 142, 144 of the feet 138, 140 of the base 130.

Also, the upper surface of each spacer block includes a centre line marking, e.g. 121, which in the illustrated embodiments is in the form of a groove, and which indicates the centre of the tibial prosthesis of the same size as the spacer block. In other embodiments, the centre line marking 121 may take other forms, for example it may be in the form of a ridge or rib, or some printed, laser marked or otherwise marked indicium.

Figures 13, 14, 15:
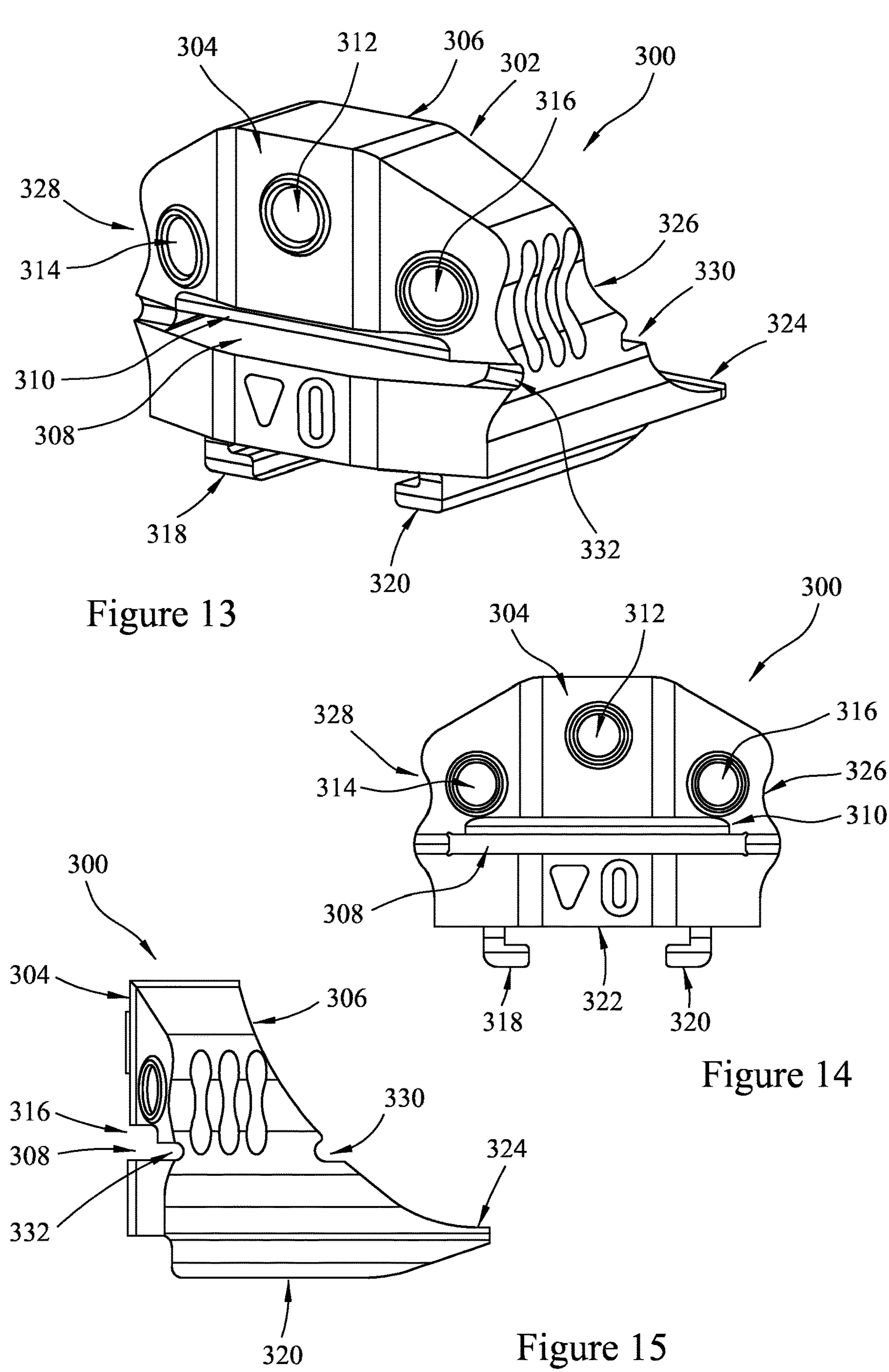
FIG. 13 shows a perspective view of a unicondylar distal cutting block.
FIG. 14 shows a front elevation of the cutting block shown in FIG. 13.
FIG. 15 shows a side elevation of the cutting block shown in FIG. 13.

FIG. 13 shows a perspective view of a unicondylar distal cutting block 300 that may be provided as part of the kit of surgical instrumentation and used in a unicondylar knee replacement procedure with the posterior cutting block described above. FIG. 14 shows a front elevation of the distal cutting block 300 and FIG. 15 shows a side elevation of the distal cutting block 300. The distal cutting block 300 has a body 302 having a front face 304 and a rear face 306. A slot 308 is defined by the body and extends from the front face through to the rear face and provides distal cutting guide for receiving a saw blade in use. A recess 310 is defined in the front face just above the mouth of the slot to aid the insertion of the saw blade.

A first, central aperture 312, a second aperture 314 to a first side and a third aperture 316 to a second side are also defined by, and extend though, the body for receiving bone screws to fix the distal cutting block in use.

A pair of opposed, inwardly directed feet 318, 320 extend from a lower surface 322 of the distal cutting block. Feet 318 and 320 and configured and dimensioned similarly to the feet of the posterior cutting block so that the distal cutting block can be mounted on the tibial spacer 120 similarly to the posterior cutting block.

A tail portion 324 of the cutting block extends from the rear side of the body. The rear surface 306 is generally curved so as approximately to replicated the curved shape of the anterior portion of a typical femoral condyle. Each side of the body defines a recessed portion, 326, 328 and a plurality of grooves are provided in the side surface of the body to facilitate grip and handling of the distal cutting block in use.

As best illustrated by FIG. 15, a portion of the side wall 330, 332 of the body adjacent the slot 308 is cut away. This allows a saw blade to be manoeuvred within the slot 308 so as to cut into lateral bone as the distal cutting block is provided in a single size and so for larger femurs the saw blade may need to be pivoted within the slot to cut through the entire distal portion of the femur.

The distal cutting block 300 illustrated in FIGS. 13 to 15 has the slot 308 positioned relative to the under surface 322, which sits on the tibial spacer block, to give rise to a default or zero off set distal cut height.

Figure 16:
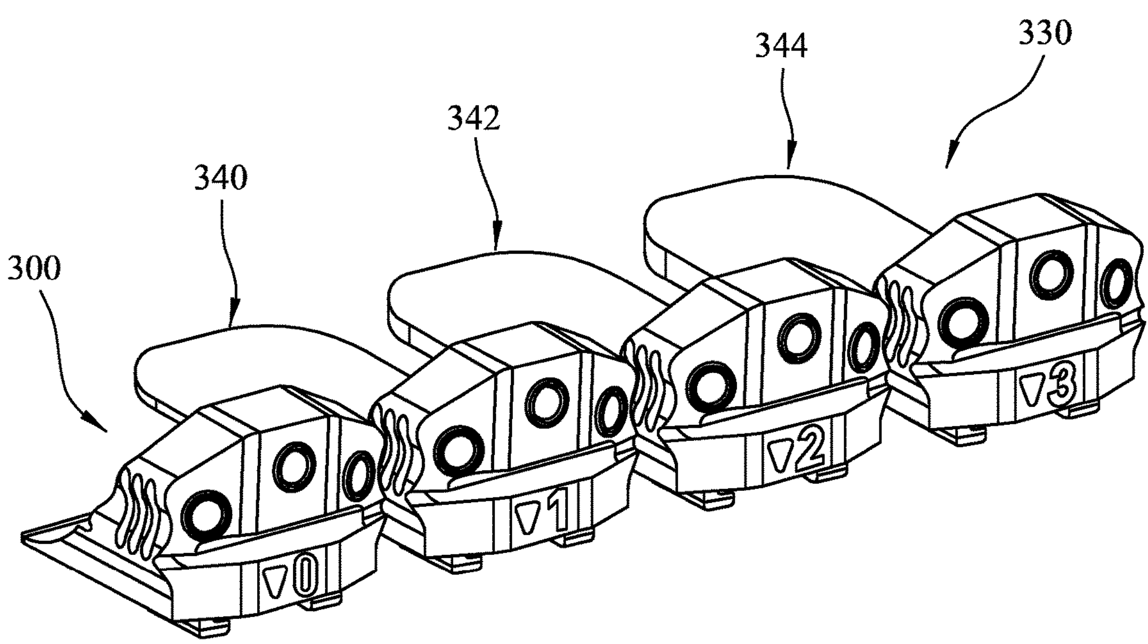
FIG. 16 shows a perspective view of a set of distal cutting blocks configured to give rise to different distal positions of the resulting distal cut.

As illustrated in FIG. 16, a range of distal cutting blocks 330 may be provided each having a cutting guide slot positioned within the body relative to the under surface at the same height, but wherein the different thicknesses of the rear tail give rise to a different distal cut off set. For example, the first distal cutting block may have a 0 mm distal cut off set and corresponds to distal cutting block 300. The second distal cutting block 340 may have a 1 mm more distal cut off set, the third distal cutting block 342 may have a 2 mm more distal cut off set, and the third distal cutting block 344 may have a 3 mm more distal cut off set. The first to fourth distal cutting blocks are generally similar except that the rear tail of the second to fourth cutting blocks extends further than that of the first cutting block and also the tails have increasing thicknesses, of 1 mm, 2 mm and 3 mm, so as to reduce the separation between the upper surface of the tail (on which the distal femur will rest in use) and the position of the slot height so as to give rise to the different distal cut offsets.

Figure 17:
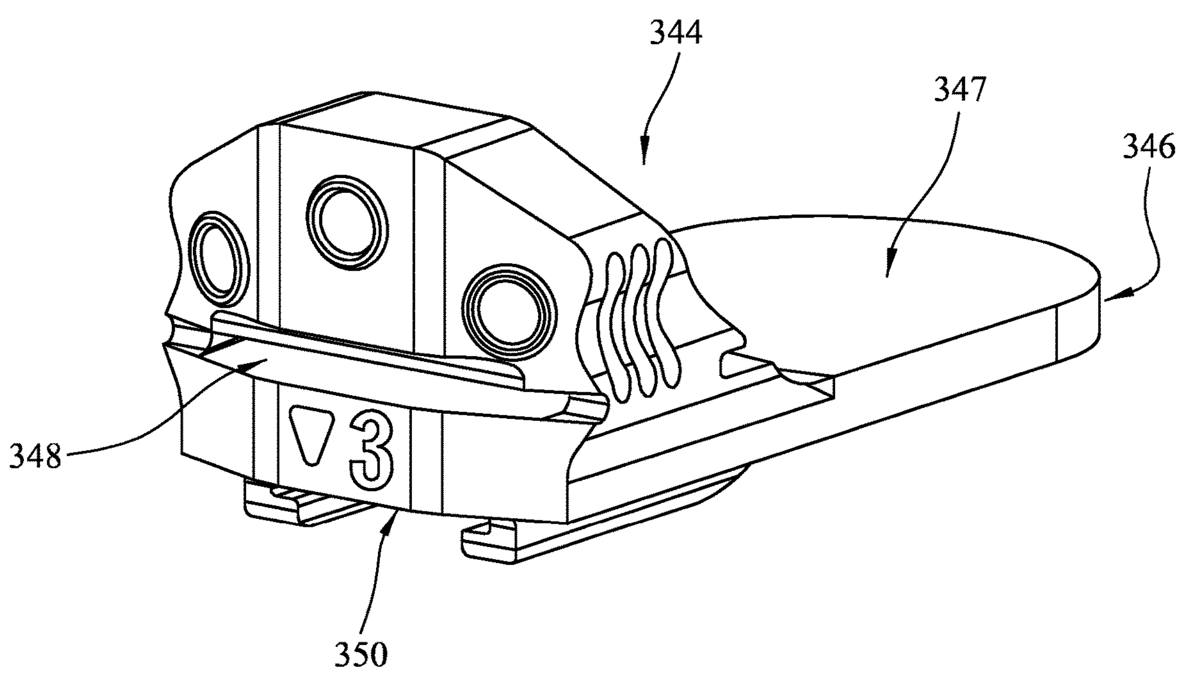
FIG. 17 is a perspective view of a one of the distal cutting blocks illustrated in FIG. 16 and giving rise to a 3 mm distal cut off set.

For example FIG. 17 shows a perspective view of the fourth distal cutting block 344 giving rise to a 3 mm distal cut off set owing to the 3 mm thickness of the rear tail 346 which moves the upper surface 347 of the rear tail 346 approximately 3 mm closer to the guide slot 348 compared to the first cutting block 300.

Figure 18:
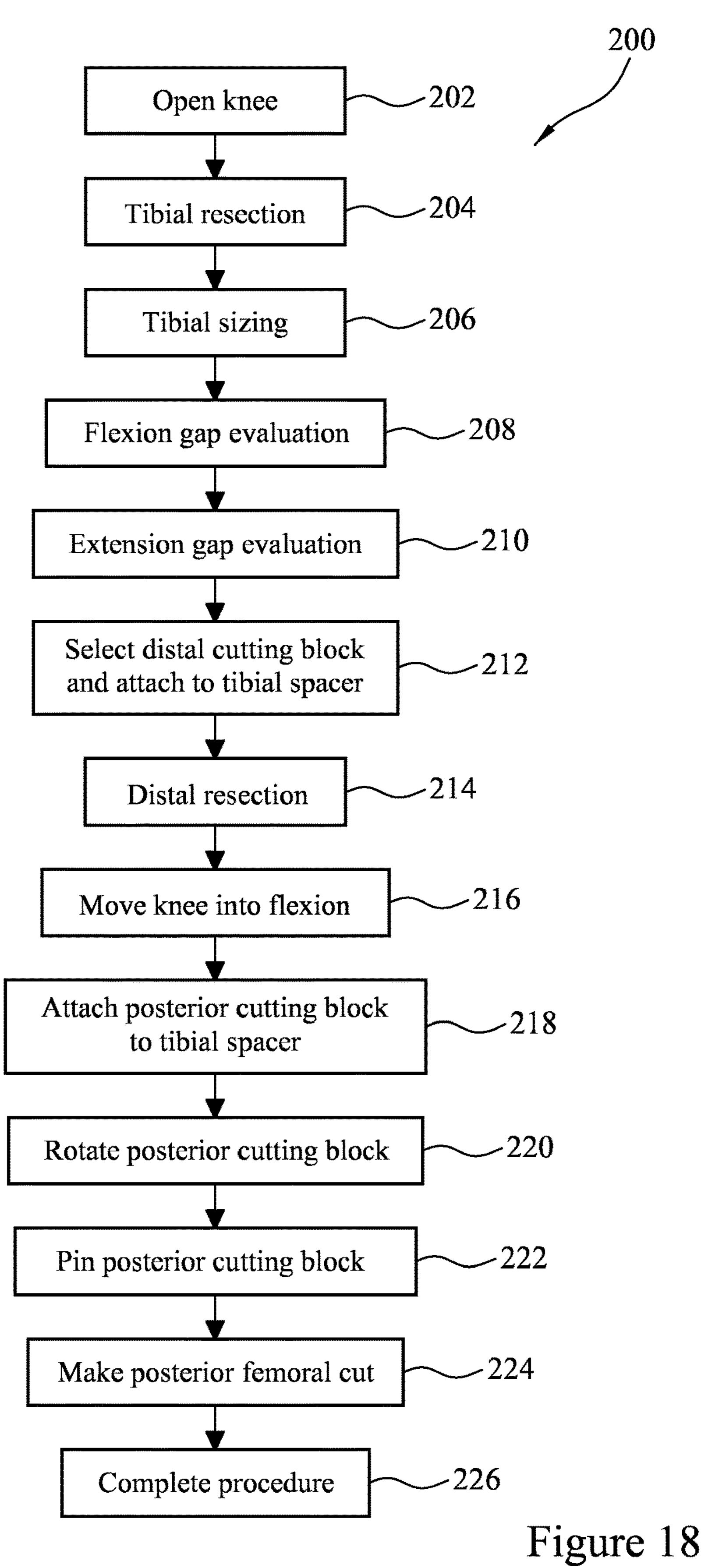
FIG. 18 shows a flow chart illustrating a partial knee replacement procedure and illustrating a method of using the surgical instrumentation to make a unicondylar posterior cut.

FIG. 18 shows a flow chart illustrating a partial knee replacement procedure 200 and including a method of use of the surgical instrumentation described above. Many of the overall steps of the procedure are conventional and hence have either been omitted or are described briefly in order not to obscure the present disclosure. The procedure is generally the same for either a medial or a lateral partial knee.

The procedure 200 described below, in relation to FIG. 18, gives priority to the knee gap in flexion rather than the knee gap in extension. The knee gap in extension is made to match the gap as measured in flexion and is generally intended to restore the joint line to the pre-disease state. A further partial knee replacement procedure 400 similar to procedure 200 will be described later, with reference to FIG. 21, and gives priority to the knee gap in extension. The knee gap in flexion is then made to match the knee gap measured in extension and is generally intended to maintain the joint line of the diseased state.

Initially the surgeon may have generally planned the procedure using pre-operative x-rays in order to estimate the likely size and positioning of the tibial and femoral implants and also the likely thickness of the tibial implant.

After any optional pre-operative templating and planning, at 202, the surgeon makes an incision to open the patient's knee to gain access to the surgical site. After exposing the surgical site, the surgeon may make an assessment of the state of the knee and the appropriate procedure to use. Also, some preparation of the surgical site may occur at 202 such as removing any soft tissue structures that are not to be preserved.

At 204 a tibial resection is made. A tibial cutting block mounted on a tibial alignment guide may be used to make the partial proximal tibial resection which is generally an L-shaped resection due to a transverse cut and subsequent sagittal cut.

At 206, the knee is placed in 90° flexion and a one of the tibial spacers of the appropriate size and with a thickness corresponding to the thickness of the tibial resection is used to check the size of the tibial resection and tibial prosthesis to be used.

After tibial sizing at 206, the knee is kept in flexion and the flexion gap is established using the spacer block of the tibial spacer at 208. Different thicknesses of spacer block may be used for the size of implant in order to establish the flexion gap to the nearest 1 mm or so. For instance, tibial spacers 208 may be provided with a range of thicknesses from 7 mm to 11 mm, in 1 mm intervals. The thickness of the spacer block represents the thickness of the tibial implant construct (tray and insert). For example, the flexion gap may be evaluated to be 7 mm. The tibial spacers may also be provided with a range of different shape and/or different area spacer blocks. For instance, six different shape and/or area spacer blocks, each also provided in two, three or four different thicknesses may be provided to form a set of tibia spacers for use. Also, with the knee in flexion, the centreline mark 121 of the spacer block is marked on the femur as a vertical line, for example using methylene blue or a diathermy mark.

After evaluating the flexion gap at 208, the knee is placed into extension and at 210 the extension gap is evaluated.

The order of assessment of the flexion gap and extension gap is not critical and in other embodiments, the extension gap may be evaluated before the flexion gap. The tibial spacer blocks are used to establish the extension gap.

The surgeon may work their way through various different thicknesses of spacer block until they feel generally the same ligament tension is achieved. Also, with the knee in extension, the centreline mark 121 is marked on the femur as a vertical line, for example using methylene blue or a diathermy mark.

If the extension gap is lax or long leg alignment requires correction, then the surgeon may use a thicker tibial spacer block to increase the extension gap to establish correct balance. For example, the extension gap may be established to be 8 mm at 210.

At 212, with the leg in extension, the distal femoral cutting block 300 to be used needs to be selected. The distal femoral cutting blocks are described above in relation to FIGS. 13 to 17.

The options for the distal femoral cutting block 300 include:

a ZERO distal cutting block used to resurface the femur as presented; for example, where the gaps are equal or the difference is less than 2 mm;

a series of further cutting blocks used to distalize the femoral resection to restore the pre-disease balance; for example where the extension gap is larger than the flexion gap, the correct cutting block can be used to close the extension gap to match the flexion gap or reduce the difference between the extension gap and the flexion gap;

Hence, the options provided in this embodiment are:

- a 1 DOWN distal cutting block to reduce the extension gap relative to the flexion gap by 1 mm;
- a 2 DOWN distal cutting block to reduce the extension gap relative to the flexion gap by 2 mm;
- a 3 DOWN distal cutting block to reduce the extension gap relative to the flexion gap by 3 mm.

As a result, there are four distal cutting block options to choose from in this example, but a wider range could be deployed.

As an example, the appropriate off set is selected based on the difference between the evaluated flexion gap (7 mm) and extension gap (8 mm) and may be used to make the distal femoral cut to the condyle being replaced. For example, as the extension gap has been evaluated to be 8 mm, whilst the flexion gap has been evaluated to be 7 mm, at 212, a distal cutting block with a 1 mm more distal off set, 1 distal cutting block, may be used to distalise the distal cut. Hence, the 1 mm off set distal cutting block 340 may be selected and attached to the 7 mm thick tibial spacer by engaging its feet in the slots of the tibial spacer and then being slid toward the tibial spacer block.

Figure 19:
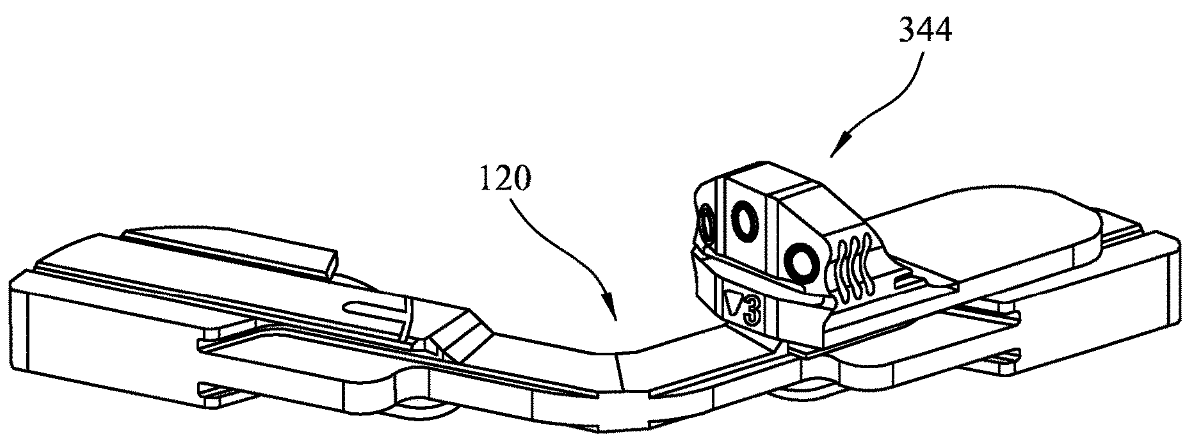
FIG. 19 shows a perspective view of a distal cutting block assembly of the surgical instrumentation used during the method illustrated in FIG. 18.

For example, an assembly of a distal cutting block mounted on the tibial spacer is illustrated in FIG. 19 although the 3 mm off set distal cutting block is illustrated in FIG. 19 rather than a 1 mm offset as being used in this example. The selected distal cutting block is mounted on the tibial spacer while the tibial spacer is mounted on the resected tibia and slid towards the anterior portion of the native condyle.

In other embodiments, the distal cutting block may be mounted on the tibial spacer and then that construct inserted into the knee gap and seared on positioned on the resected tibia. The knee may need to be flexed slightly to ensure that the distal resection is parallel to the tibial resection.

With the correct distal cutting block selected and inserted, the distal tibial cutting block is then pinned in place using bone screws in one or more of the pinning apertures 312, 314, 316 and then the distal femoral cut may be made using a bone saw, with the knee in extension.

After unpinning, the distal cutting block and spacer may be removed and the distal cutting block may be removed from the tibial spacer by being slid down and then removed from the tibial spacer.

At 216 the knee is moved into hyperflexion, for example into a flexion angle of approximately 105°. If the knee is not placed in hyperflexion, then it can be difficult to configure a posterior cutting block to permit the posterior cut to be made with a bone saw without the saw impinging with the cutting block.

Then, at 218, the appropriate posterior cutting block 110, as described above in FIGS. 1 to 10, is selected and attached to the same tibial spacer as used to make the distal cut (a 7 mm thickness tibial spacer block in this example) so as to mount the cutting block indirectly onto the resected tibial surface, via the spacer 124.

Figure 20:
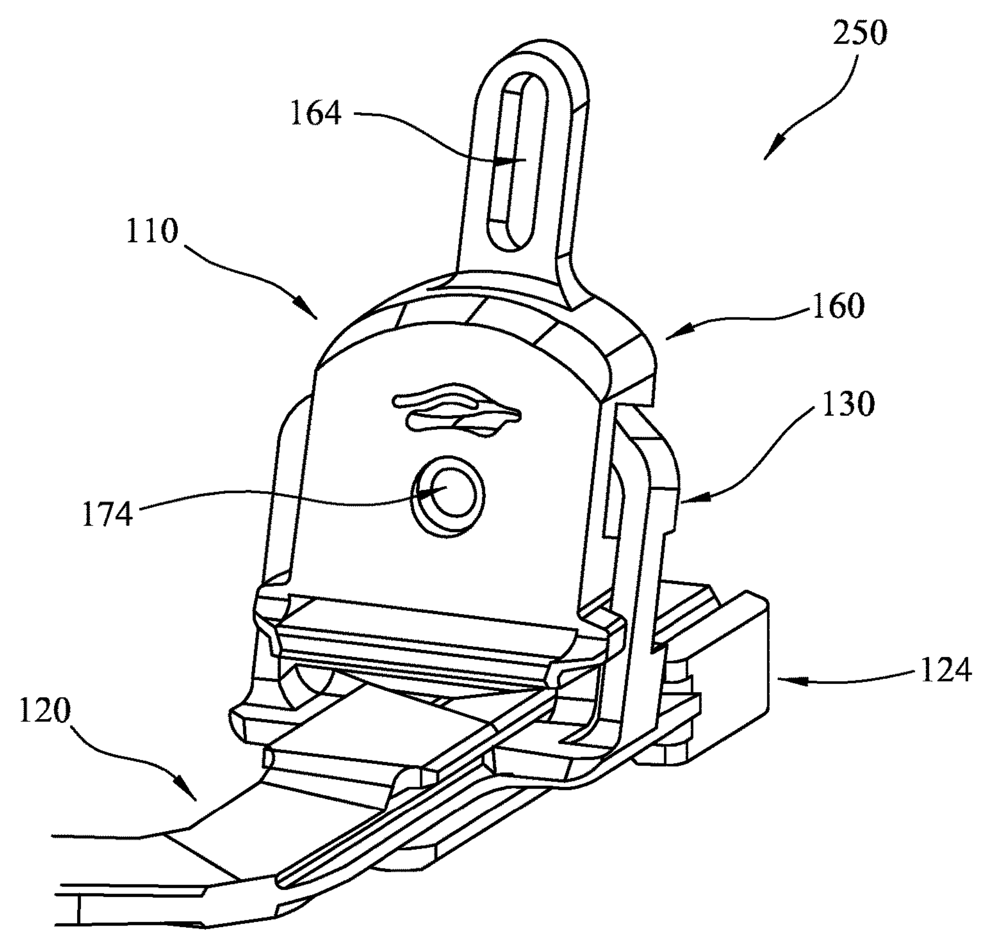
FIG. 20 shows a perspective view of a posteriori cutting block assembly of the surgical instrumentation used during the method illustrated in FIG. 18.

The options for the posterior cutting block 300 include:

a 1 DOWN cutting block, which can:

after use of the ZERO distal cutting block, maintain the flexion gap;

a ZERO cutting block, which can:

after use of the ZERO distal cutting block, open up the flexion gap; or after use of the 1 DOWN, 2 DOWN or 3 DOWN distal cutting block, leave 1 mm of laxity in flexion;

a 1 UP cutting block, which can:

after use of the ZERO distal cutting block, open up the flexion gap;

For example, in the current example, as a 7 mm flexion gap is required, then the 0 mm offset posterior cutting block 160 is selected and mounted on the 7 mm thick tibial spacer block. Specifically, the base 130 is placed on the tibial spacer and the ribs 142, 144 of feet 138, 140 are engaged with the slots 127, 129 on either side of the tibial spacer. The cutting block 160 is then slid along the tibial spacer toward the distal resection of the femur until the rear of the cutting block abuts the distal femoral resection, as illustrated in FIG. 20 which shows the assembly 250 of the cutting block 110 on the tibial spacer 120 and positioned adjacent the distal resection of the femur (not shown).

At 220, the body of the cutting block is rotated by hand until the extended member 162 is aligned parallel to the centre line marking made previously and hence aligned with the rotation of the femur. The elongate slot may be used to help guide rotation of the body until parallel to the centre line marking on the femur made previously.

At 222, the cutting block is pinned in place using either a bone pin passing through the slot 164 or a bone pin passing through the centre aperture 174, or both. The extended slot 164 as well as helping to establish alignment with the centre line marking also permits the surgeon to pick a preferred part of the bone to pin to, if other parts are less good pining sites.

Then at 224, the posterior femoral cut may be made using a bone saw guided by the cutting guide slot 168 of the cutting block. By rotating the body and hence the cutting slot of the cutting block so as to be perpendicular to the centre line marked previously, this helps to ensure that the gap size in flexion will be kept closer to the target 7 mm value notwithstanding the internal rotation of the femur.

If, after completing the first cut, the flexion gap is found to be too tight, then recutting of the posterior condyle is possible. For instance, to remove a further 1 mm:

if the 1 DOWN cutting block was used to make the cut, then the ZERO cutting block would be used to make the recut;

of the ZERO cutting block was used to make the cut, then the 1 UP cutting block would be used to make the recut.

Once the posterior cut has been completed, the cutting block may be de-pinned and the tibial spacer and cutting bock construct may be removed from the knee. The surgical procedure may then continue in a generally conventional manner at 226 until the partial knee replacement has been completed. The further parts of the procedure may include completing femoral preparation by making any chamfer cuts required for the femoral implant, trialling, keel preparation for the tibial implant, cement pressurisation (for a cemented implant system) and finally a polymer bearing surface insert.

Figure 21:
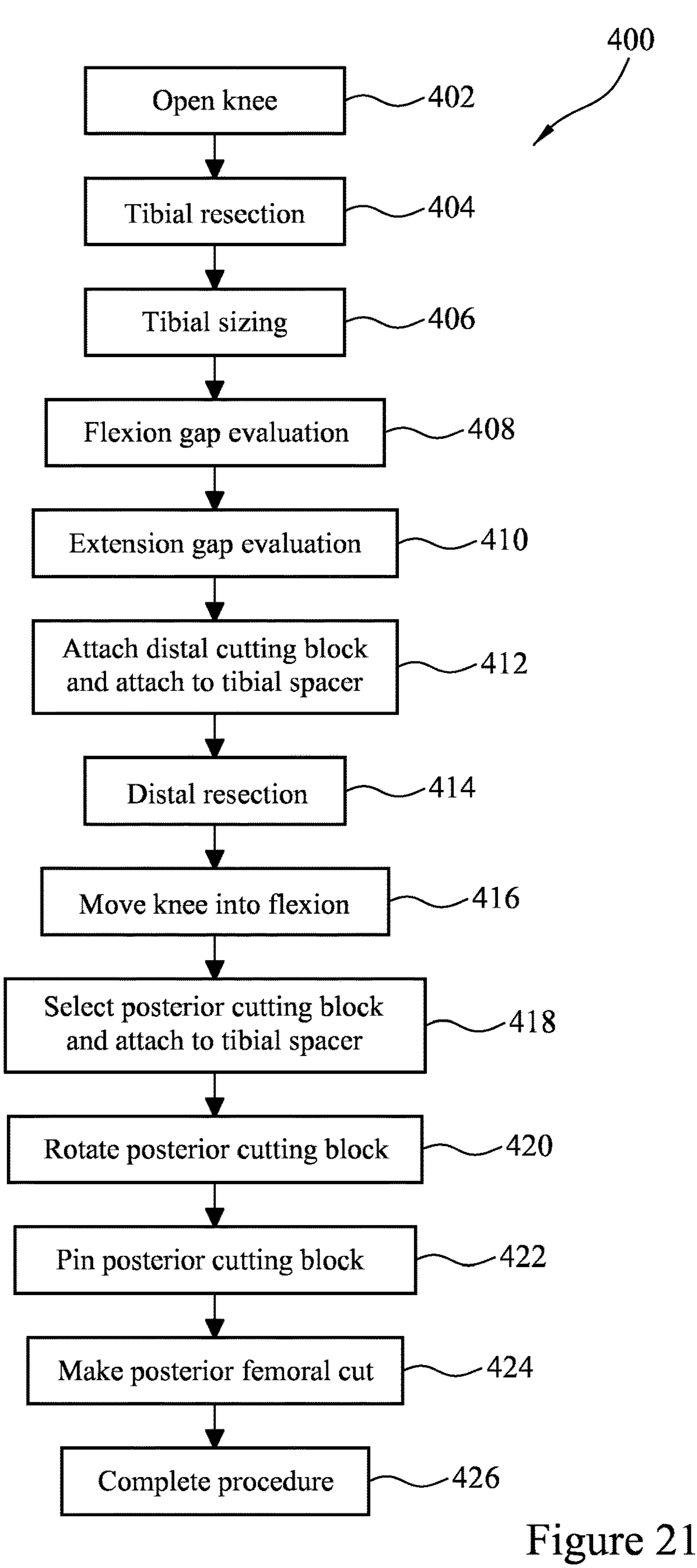
FIG. 21 shows a flow chart illustrating a partial knee replacement procedure and illustrating a further method of using the surgical instrumentation to make a unicondylar posterior cut.

FIG. 21 shows a flow chart illustrating a further unicondylar knee replacement procedure 400 generally similar to procedure 200 but prioritising the extension gap. Many of the steps are generally similar to those of the flexion gap prioritising procedure 200 and so will not be described again in detail.

Following evaluation of the flexion gap 408, which may be for example 7 mm and marking of the vertical centre line on the femur, the extension gap is evaluated at 410 and again the vertical centre line marked on the femur. For example, the extension gap may be evaluated to be 9 mm. Again, the order of evaluation of the flexion gap and extension gap is not important and may be reversed. If the extension gap is lax or long leg alignment requires further correction, then thicker spacer blocks may be used to increase the extension gap to establish correct balance.

At 412, in the example, the 0 mm off set distal cutting block, ZERO distal cutting block, is selected and attached to the 9 mm tibial spacer block inserted in the knee gap. The knee may need flexing slightly to ensure that the distal resection is parallel to the tibial cut. The distal cutting block is pinned in position and then the distal femoral cut is made at 414. The distal cutting block is then removed and the knee is placed in hyperflexion again at 416.

If the extension gap is loose, then different distal cutting blocks can be chosen to adjust the resection level and depth of bone removed; the 1 DOWN, 2 DOWN and 3 DOWN will each remove 1 mm less than the previous one as the block shim thickness in each is 1 mm greater than in the previous one.

To select the posterior cutting block to use at 418, the difference between the extension gap and the flexion gap is used, in this case 9 mm minus 7 mm which is approximately 2 mm. Hence, the 2 mm offset posterior cutting block is selected so as to anteriorise the posteriori cut (i.e. move the posteriori cut in the anterior direction) by approximately 2 mm. The posterior cutting block is then attached to the same 9 mm tibial spacer block and slid toward the resected distal femur. The body of the cutting block is then rotated at 420 until the elongate slot 164 is parallel to the vertical centre line marked previously. The posterior cutting block is then pinned in place at 422 using the elongate slot 164 and/or the centre pinning aperture 174. The posterior femoral cut is then made at 424, and then the rest of the procedure can be completed in the same way as described generally above.

Using the pivoting cutting guide slot may help to avoid unintended effects on soft tissue tension compared to other posteriori cutting blocks. For example if the cutting block references the femoral posterior condyle then the cutting block will track this bone surface during any femoral rotation which moves the cutting block relative to the tibia, for example toward the tibia, which may result in an unexpected tightness of the joint in flexion, or away from the tibia which may result in unexpected laxity of the joint in flexion. Hence, the pivotable cutting guide slot driven by the camming surface of the curved member which has been mounted on the resected tibia maintains the height of the posterior cut as internal rotation is applied. Hence, the surgeon's laxity preference can be maintained regardless of how much rotation they choose to apply. The posterior cut will generally be parallel to the tibial resection at the intended femoral rotation and therefore the knee gap size will be maintained.

With respect to both the distal cutting block and then the posterior cutting block, the user has to make a selection from amongst the set of options for that block that are offered. As explained above, the distal cutting block options could include a zero mm, 1 mm, 2 mm and 3 mm options with the mm values reflecting the extent to which the cut is distalized. Also as explained above, the posterior cutting block could offer a zero mm, plus 1 mm and minus 1 mm options to control the laxity provided. It is useful for the user to be able to quickly and accurately judge which option to select to achieve the desired effect.

It would be possible to mark each instrument with a numerical indication of the variance and a positive or negative sign to indicate the nature of the variance. However, such an approach is not so intuitive or clear as might at first seem on what the selection is doing to the cut. For instance, does the positive indicia relate to a cut that is further up the bone or to a cut that is further down and so removes more bone?

Rather than use a value and sign [positive or negative] indicia, embodiments of the invention take an alternative approach. As shown in FIG. 16, a graphical indicia 500 is provided which indicates the vector of the variation. This is accompanied by a numerical indicia 502 which indicates the extent of the variation.

Thus, referring to FIG. 16, a set of distal cutting blocks is shown from which the selection is to be made by the user. Having reached distal cutting block selection step 212, in the methodology of FIG. 18, the user has established the flexion gap through the flexion gap evaluation 208 and the extension gap through extension gap evaluation 210. A similar position applies, with respect to the methodology of FIG. 21, once steps 408 and 410 have been completed to provide the evaluations there. Based upon the flexion gap and the extension gap, the user will have in mind the adjustment they want to achieve. For instance, where the extension gap is larger than the flexion gap, relative to an acceptable variation, then the correct cutting block can be used to close the extension gap to match the flexion gap or reduce the difference between the extension gap and the flexion gap.

For example, the acceptable variation might be 0 mm to 2 mm, and the observed difference in gaps might be 3 mm, with the user deciding to apply a 2 mm reduction in the difference between the gaps. Thus, the user needs to select the right distal cutting block for the determined gap reduction.

Referring to the instrument tray or other location where the set of distal cutting blocks is set out, the user is presented with a clear indication and confirmation by the graphical indicia that the numerical indicia is a reduction in the gap difference. The graphical indicia points downward to indicate a reduction. That this direction is downwards is clearly confirmed by the adjacent numerical indicia which has a readily understandable orientation to the user. Thus, selection of the distal cutting block with the numeral indicia 2 and the graphical indicia which is downward in the information it conveys, means that the user has selected the correct distal cutting block.

By providing the numerical indicia and the graphical indicia adjacent to the slot 308 which receives the saw when cutting, the numerical indicia and the graphical indicia are visible during their insertion into the gap and during the operative steps that they are involved with. Thus, verification of the intended distal cutting block being used can be provided at any time.

Whilst positioned prior to selection, for instance in an instrument tray, the distal cutting blocks may be positioned side on so as to show the relative thicknesses [in the case of 1 DOWN, 2 DOWN and 3 DOWN] of the spacer or to show the absence in the case of ZERO DOWN] of the spacer, to assist in selection, with the graphical indicia and numerical indicia being verified on lifting from the position prior to use. Alternatively, the distal cutting blocks may be orientated to show the graphical indicia and numerical indica upwards.

After the completion of the distal resection, 214 in FIGS. 18 and 414 in FIG. 21, both alternative methods move on to the selection of the posterior cutting block, steps 218 and 418 respectively. Based upon the flexion gap and the extension gap evaluations, the nature of the distal resection, and whether flexion gap or extension gap is to be prioritised, the user will have in mind the adjustment they want to achieve. For instance, the user might decide that the flexion gap and extension gap having been adjusted for by the distal cutting block, are as desired and that no further adjustment is needed.

As an example, as a result of the 2 mm adjustment described above, the desired difference between the flexion gap and the extension gap would have been restored to within the acceptable range. In that case, no further adjustment would be needed via the posterior cutting block. Referring to the set of posterior cutting blocks presented in FIGS. 22*a*, 22*b* and 22*c*, this would result in the ZERO posterior cutting block of FIG. 22*b* being selected. The ZERO posterior cutting block is configured to provide no further adjustment and has 1 mm of laxity in flexion built into its configuration.

Figures 22A, 22B, 22C:
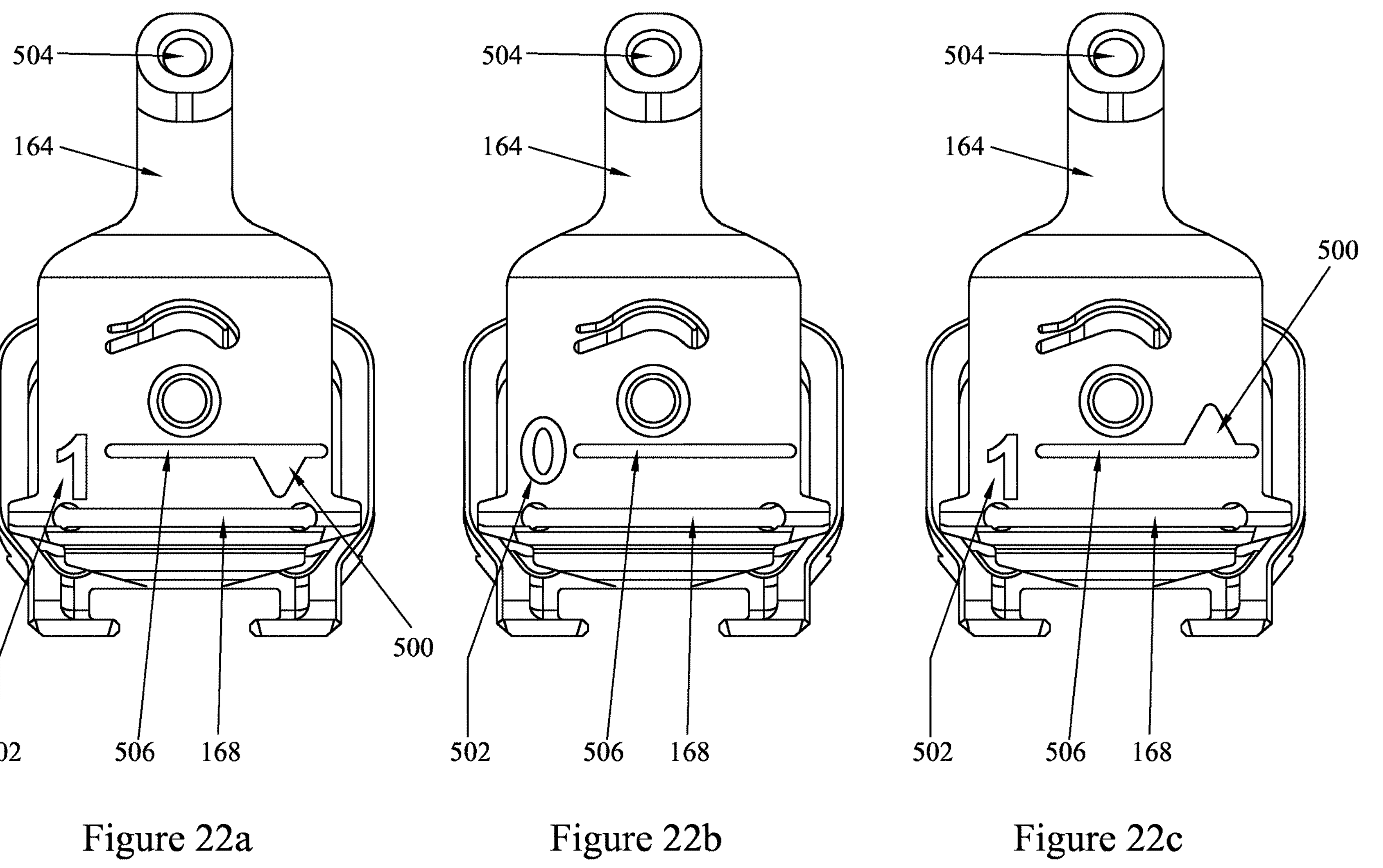
FIGS. 22*a*, 22*b* and 22*c* are front elevations of three further cutting blocks each having a different body corresponding to a different amount of off set of the posterior cut and providing graphical indicia and numerical indicia.

As an alternative, if there was a need to prioritise the extension gap, or if increased laxity was otherwise needed, then an increase would be sought. In that case, the user would need to select an increasing gap posterior cutting block relative to the distal cutting block and/or relative to the posterior cutting block just used. FIG. 22*c* is an example of such a posterior cutting block. If the laxity was too high, then the user would need to select a decreasing gap posterior cutting block; as illustrated in FIG. 22*a*.

Referring to the instrument tray or other location where the set of posterior cutting blocks is set out, the user is presented with a clear indication and confirmation by the graphical indicia on what the numerical indicia is referring to. The ZERO value numerical indicia 502 and absence of a graphical indicia 500 pointing in either direction confirms that this is the correct option for no further adjustment. The numerical indicia 502 value of 1 and the graphical indicia 500 pointing downward is a confirmation that this is a reduction in gap in the FIG. 22*a* example. That this direction is downwards is clearly confirmed by the numerical indicia 502, which is graphically linked to the graphical indicia 500 by further graphical indicia element 506, with the numerical indicia 502 having a readily understandable orientation to the user. Similarly, the numerical indica 502 value of 1 and the graphical indicia 500 pointing upward, FIG. 22*c*, is a confirmation that this is an increase in gap. Thus, selection of the posterior cutting block desired is made easier.

The further graphical indicia element 506 assists in the interpretation of the indicia by providing a clear connection between the numerical indicia 502 and the graphical indicia 500. The further graphical indicia element 506 also reinforces that the graphical indicia 500 indicates an increase or decrease with respect to the cutting plan of slot 168 by the further graphical indicia element 506 running parallel to that slot 168 and hence consist with the cutting plane that would be varied.

The numerical indicia 502, graphical indicia 500 and the further graphical indicia element 506 are recessed relative to the surrounding surface in the FIG. 22*a-c* embodiments. This assists with their clear viewing by the user. Protruding indicia and/or surface alterations, such as surface texture can be used to form or partially form the indicia.

By providing the numerical indicia and the graphical indicia adjacent to the slot 168 which receives the saw when cutting, the numerical indicia 502 and the graphical indicia 500 are once again visible during their insertion into the gap and during the operative steps that they are involved with.

Thus, verification of the intended posterior cutting block being used can be provided at any time.

Whilst positioned prior to selection, for instance in an instrument tray, the posterior cutting blocks may be orientated with the graphical indicia 500 and numerical indica 502 upwards and hence highly visible when inspected.

In this specification, example embodiments have been presented in terms of a selected set of details. However, a person of ordinary skill in the art would understand that many other example embodiments may be practiced which include a different selected set of these details. It is intended that the following claims cover all possible example embodiments.

Any instructions and/or flowchart steps can be executed in any order, unless a specific order is explicitly stated. Also, those skilled in the art will recognize that while one example set of instructions/method has been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are covered as well.

The invention claimed is:

1. A unicondylar posterior cutting block comprising:

a base which is mountable on a resected proximal tibial surface of a knee of a patient in use with the patient's knee in flexion; and a body pivotally attached to the base, the body including an alignment formation arranged to align with a marking on a femur in use, the body defining a cutting guide therein for receiving a cutting instrument to make a unicondylar posterior cut in the femur and wherein the body is configured to rotate relative to the base and tilt the cutting guide relative to the base when the alignment formation is moved to align with the marking on the femur.

2. The cutting block of claim 1, wherein the body is connected to the base by a pivot defining an axis of rotation.

3. The cutting block of claim 2, wherein the base includes a curved member over which the body rides when pivoting.

4. The cutting block of claim 2, wherein the formation defines an elongate slot extending along a slot axis and wherein the slot axis passes through the axis of rotation or wherein the formation is a through aperture.

5. The cutting block of claim 3, wherein the curved member has a non-constant radius of curvature and wherein the pivot can translate relative to the base as the body rides over the curved member.

6. The cutting block of claim 3, wherein the curved member has a first shoulder at a first end and a second should at a second end.

7. The cutting block of claim 3, wherein the body includes a resilient biasing member arrange to maintain contact between the curved member and a part of the body.

8. The cutting block of claim 3, wherein the body includes a fixing arranged to capture the curved member within a part of the body.

9. A unicondylar posterior cutting block comprising:

a base which is mountable on a resected proximal tibial surface of a knee of a patient in use; and a body pivotally attached to the base, the body including an alignment formation arranged to align with a marking on a femur in use, the body defining a cutting guide therein for receiving a cutting instrument to make a unicondylar posterior cut in the femur and wherein moving the alignment formation to align with the marking on the femur causes the body to rotate relative to the base and to tilt the cutting guide relative to the base, wherein a rear face of the cutting block defines a first plane, and the cutting guide defines a second plane and wherein the first plane and the second plane subtend an acute angle of less than 80°.

10. The cutting block of claim 1, wherein the body defines a circular aperture extending therethrough for receiving a bone pin.

11. The cutting block of claim 1, wherein the base includes feet by which the base is releasably attachable to a tibial spacer.

12. The cutting block of claim 9, wherein the base includes feet by which the base is releasably attachable to a tibial spacer.

13. A method for making a unicondylar posterior cut to a femur of a knee of a patient, comprising:

positioning a unicondylar posterior cutting block on a resected proximal tibial surface of a tibia of the knee of the patient and adjacent a distally resected condyle of a femur of the knee of the patient and with the knee in flexion, wherein the cutting block comprises a base and a body, the body being rotatable relative to the base and the body defining a cutting guide therein;

aligning an alignment feature attached to the body with a marking on the femur to rotate the body relative to the base;

fixing the body to the femur; and using the cutting guide to make a posterior femoral cut with a cutting tool.

14. The method of claim 13, further comprising:

mounting the unicondylar posterior cutting block on a tibial spacer and wherein the tibial spacer is placed on the resected proximal tibial surface.

15. The method of claim 13, wherein mounting the cutting block on the tibial spacer comprises:

mounting the cutting block on the tibial spacer at a first position; and moving the cutting block along the tibial spacer from the first position toward the femur.

16. The method of claim 13, and further comprising:

selecting the unicondylar posterior cutting block from a plurality of unicondylar posterior cutting blocks, each of the plurality of unicondylar posterior cutting blocks defining a respective cutting guide having a different position corresponding to a different anterior position or a different cut extent of the posterior cut.

17. The method of claim 13, and further comprising:

mounting a unicondylar distal cutting block on a tibial spacer; and using the unicondylar distal cutting block to make a distal femoral cut.

18. The method of claim 17, wherein the method further comprises:

selecting the unicondylar distal cutting block from a plurality of unicondylar distal cutting blocks, each of the plurality of unicondylar distal cutting blocks defining a respective cutting guide having a different position corresponding to a different distal position of the distal cut.

19. The method of claim 13, further comprising:

evaluating a flexion knee gap between a posterior part of a native condyle of the femur and a proximal resection of the tibia with the knee in flexion;

evaluating an extension knee gap between a distal part of the native condyle and the proximal resection of the tibia with the knee in extension; and making a distal femoral cut at a distal position of the native condyle that will make the resulting knee gap in extension match the flexion knee gap.

20. The method of claim 13, further comprising:

evaluating a flexion knee gap between a posterior part of a native condyle of the femur and a proximal resection of the tibia with the knee in flexion;

evaluating an extension knee gap between a distal part of the native condyle and the proximal resection of the tibia with the knee in extension; and making the posterior femoral cut at an anterior position of the native condyle that will make the resulting knee gap in flexion match the extension knee gap.

* * * * *